United States Patent [19]
Wilkening

[11] Patent Number: 5,189,159
[45] Date of Patent: Feb. 23, 1993

[54] 8A-AZA-8A-HOMOERYTHROMYCIN CYCLIC IMINOETHERS

[75] Inventor: Robert R. Wilkening, Maplewood, N.J.

[73] Assignee: Merck & Co., Inc., Rahway, N.J.

[21] Appl. No.: 859,263

[22] Filed: Apr. 2, 1992

[51] Int. Cl.[5] .................. A61K 31/95; C07D 521/00
[52] U.S. Cl. .................................. 540/456; 514/183; 514/450
[58] Field of Search ...................................... 540/456

[56] References Cited

U.S. PATENT DOCUMENTS

| | | | |
|---|---|---|---|
| 3,869,444 | 3/1975 | Freiberg | 540/468 |
| 3,979,511 | 9/1976 | Hung et al. | 540/468 |
| 4,152,424 | 5/1980 | Kierstead et al. | 540/468 |
| 4,328,334 | 5/1982 | Kobrihel et al. | 514/29 |
| 4,349,545 | 9/1982 | Gouin d'Ambrieres et al. | 540/468 |
| 4,465,674 | 8/1984 | Bright et al. | 540/468 |
| 4,492,688 | 1/1985 | Bright | 514/29 |
| 4,512,982 | 4/1988 | Hauske et al. | 514/29 |
| 4,517,359 | 5/1988 | Kobrehel et al. | 540/468 |
| 4,518,590 | 5/1988 | Hauske et al. | 514/29 |
| 4,526,889 | 7/1988 | Bright | 54/29 |
| 4,680,386 | 7/1989 | Morimoto et al. | 540/486 |
| 4,886,792 | 12/1989 | Djokic et al. | 540/468 |
| 4,921,839 | 5/1990 | Brain et al. | 540/488 |
| 4,957,905 | 9/1990 | Hunt | 340/468 |
| 4,990,602 | 2/1991 | Morimoto et al. | 540/468 |

FOREIGN PATENT DOCUMENTS

| | | | |
|---|---|---|---|
| 0101186 | 2/1984 | European Pat. Off. | 514/29 |
| 0109253 | 5/1984 | European Pat. Off. | 540/468 |
| 0109253 | 5/1984 | European Pat. Off. | 540/467 |
| 0136831 | 4/1985 | European Pat. Off. | 514/29 |
| 0259789 | 3/1987 | European Pat. Off. | 514/29 |
| 0283055 | 9/1988 | European Pat. Off. | 540/468 |
| 0298650 | 1/1989 | European Pat. Off. | 514/29 |
| 0307128 | 3/1989 | European Pat. Off. | 540/468 |
| 0316128 | 5/1989 | European Pat. Off. | 514/29 |
| 0340990 | 11/1989 | European Pat. Off. | 514/29 |

OTHER PUBLICATIONS

Journal of Antibiotics, vol. 40, No. 7, by S. Djokic et al., (Jul. 1987).
J. Chem. Soc. Perkin Trans. 1, pp. 1881-1890, by S. Djokic et al. (1986).
J. Chem. Research (S), pp. 152-153, by S. Djokic et al. (1988).
The Journal of Antibiotics, vol. 61, No. 8, pp. 1029-1047, by Bright et al. (1988).
Tetrahedron Letters, No. 2. pp. 157-160 by E. H. Massey et al., (1970).
The Journal of Antibiotics, vol. 44, No. 3, J. C. Gasc et al. pp. 313-329 (1990).
Antimicrobic Newsletter, vol. 4, No. 4 (1987) Thornsberry et al., pp. 25-36.
Puar et al., *SCH 23831, A Novel Macrolide From Micromonospora Rosaria*, Tetrahedron Letters No. 30, pp. 2767-2770 (1979).

*Primary Examiner*—Robert T. Bond
*Attorney, Agent, or Firm*—Frank P. Grassler; Joseph F. DiPrima

[57] ABSTRACT

Cyclic iminoethers of the general structural formula wherein one of the R groups is hydrogen and the other R group represents a bond between the oxygen atom at C-6 or C-12 and the imino carbon at C-9;

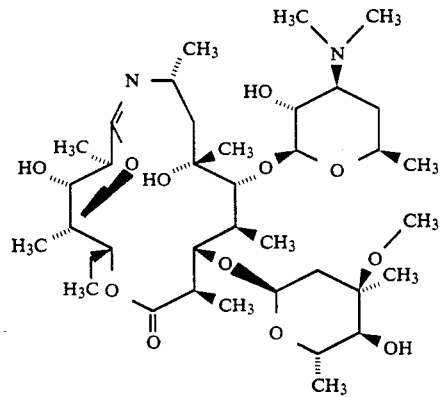

and

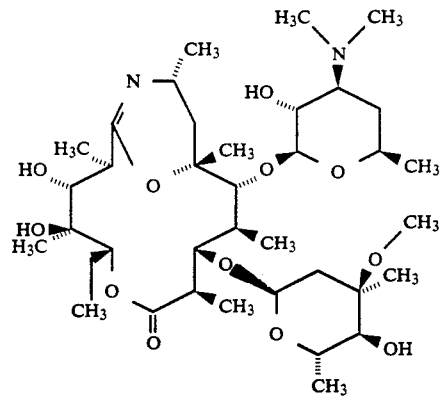

These compounds are macrolides useful as antibiotics and as intermediates for the synthesis of other macrolide antibiotics.

3 Claims, No Drawings

8A-AZA-8A-HOMOERYTHROMYCIN CYCLIC IMINOETHERS

BACKGROUND OF THE INVENTION

The present invention relates to a novel group of chemical compounds having antibacterial activity, which are useful in the therapy of bacterial infections in mammals. The compounds themselves are also useful as intermediates in the synthesis of other antibacterial compounds. More specifically, the invention relates to derivatives of the well-known macrolide antibiotic, erythromycin A, the compound of the structure:

(I)

Even more specifically, the invention relates to the compounds of the structure:

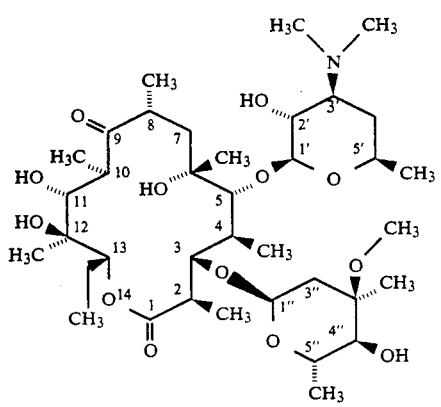

and

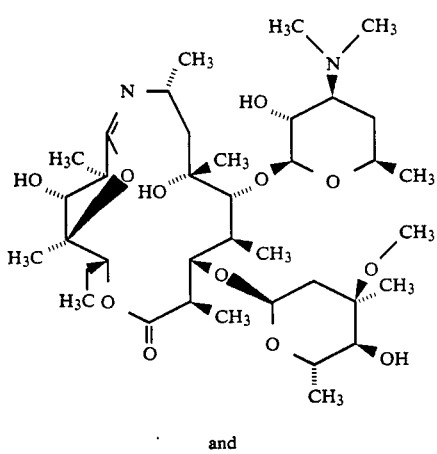

and

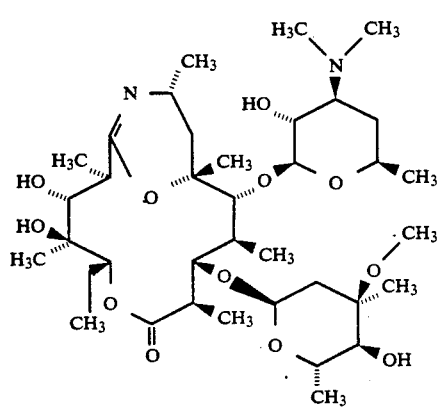

The present invention also provides for novel pharmaceutical compositions and methods of their use as antibiotic agents.

SUMMARY OF THE INVENTION

The present invention relates to novel compounds, cyclic iminoethers, that are bicyclic. The first cyclic structure is a 15-membered macrolide, while the second cyclic structure is an iminoether bridging the macrolide at either the 6,9 positions or the 9,12 positions as shown in the following structures:

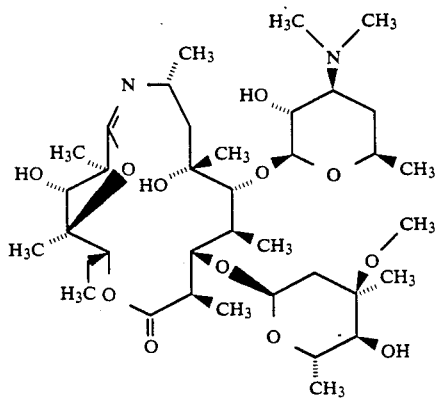

and

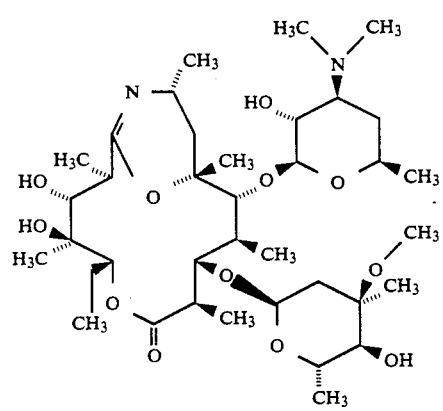

The invention includes the pharmaceutically acceptable salts of the compounds shown above. Such salts are generally prepared as acid addition salts by combining the compound of formula II with a stoichiometric amount of an appropriate acid in an inert solvent, and then the salt is recovered by solvent evaporation or by filtration if the salt precipitates spontaneously, or by precipitation using a co-solvent or a non-polar co-solvent followed by filtration.

Representative salts include the following salts:

Acetate
Benzenesulfonate
Benzoate
Bicarbonate
Bisulfate
Bitartrate
Borate
Bromide
Calcium Edetate
Camsylate
Carbonate
Chloride
Clavulanate -continued Citrate
Dihydrochloride
Edetate
Edisylate
Estolate
Esylate
Ethylsuccinate
Fumarate
Gluceptate
Glucoheptonate
Gluconate
Glutamate
Glycollylarsanilate
Hexylresorcinate
Hydrabamine
Hydrobromide
Hydrochloride
Iodide
Isothionate
Lactate
Lactobionate
Laurate
Malate
Maleate
Mandelate
Mesylate
Methylsulfate
Mucate
Napsylate
Nitrate
Oleate
Oxalate
Pamoate (Embonate)
Palmitate
Pantothenate
Phosphate/diphosphate
Polygalacturonate
Salicylate -continued Stearate
Subacetate
Succinate
Tannate
Tartrate
Teoclate
Tosylate
Triethiodode
Valerate

DETAILED DESCRIPTION OF THE INVENTION

The term "pharmacologically effective amount" shall mean that amount of a drug or pharmaceutical agent that will elicit the biological or medical response of a tissue, system or animal that is being sought by a researcher or clinician.

the term "antibiotically effective amount" shall mean that amount of an antiobiotic compound that will achieve a level of antibacterial activity at the site of infection that is sufficient to inhibit the bacteria in a manner that allows the host organism to overcome the infection.

The compounds of formula II can be prepared readily according to the following schemes, detailed descriptions and examples or modifications thereof using readily available starting materials, reagents and conventional synthesis procedures. The overall process is illustrated in the following flow sheet. In these reactions, it is also possible to make us of variants which are themselves known to those of ordinary skill in this art, but which are not mentioned in greater detail.

FLOW SHEET

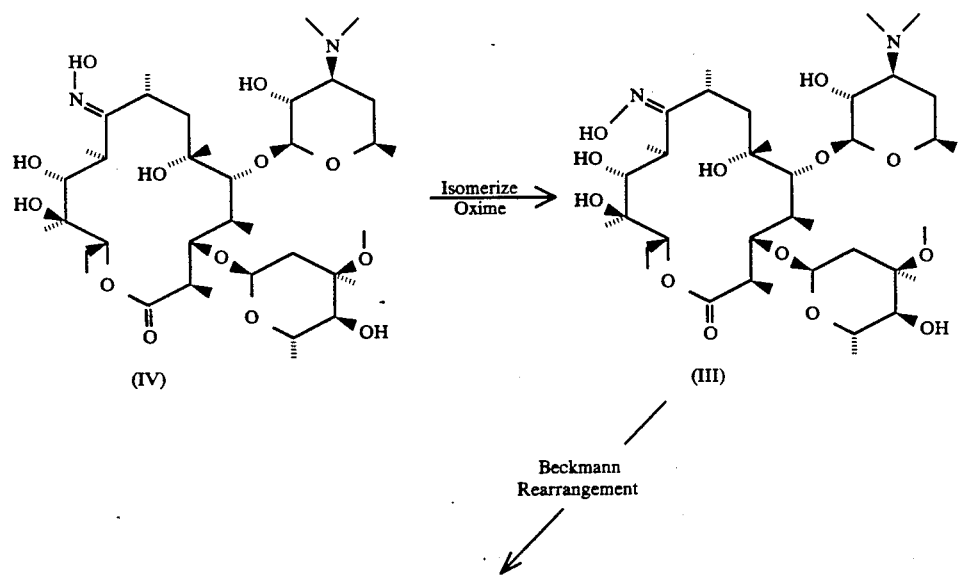

-continued
FLOW SHEET

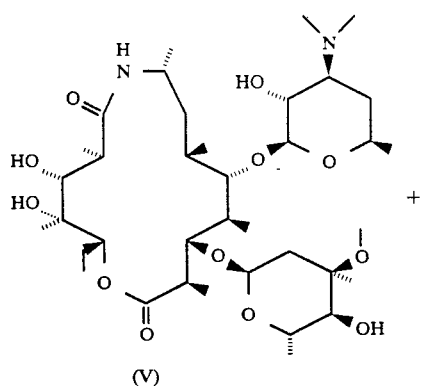

(V)

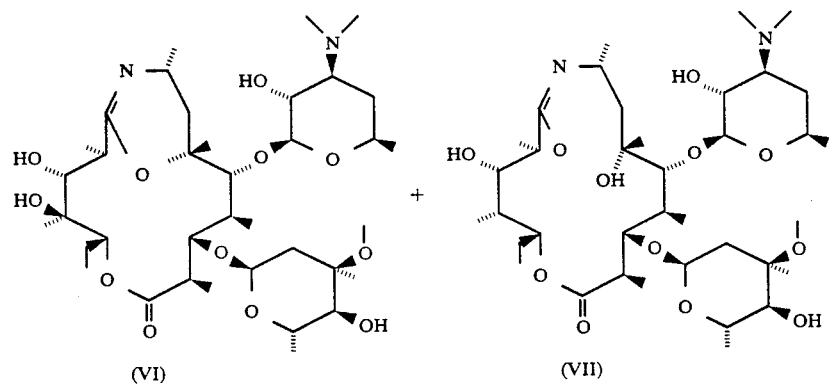

(VI)        (VII)

Isomerization of (9E)-Deoxo-(-hydroximinoerythromycin A to the (9Z) isomer

In a single step procedure, (9Z)-9-deoxo-9-hydroxyiminoerythromycin A of the structure:

(III)

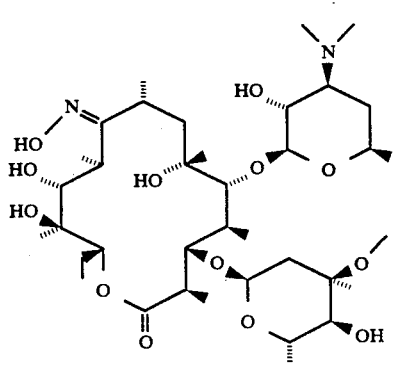

is obtained by reacting a (9E)-9-deoxo-9-hydroxyiminoerythromycin A of the structure:

(IV)

with a base in the presence of a protic or an aprotic solvent. Preferably, the base is an alkali metal hydroxide and the solvent is an alcohol. Most preferably, the base is lithium hydroxide (as the monohydrate) and the solvent is ethanol.

Optimization of the method of the isomerization step requires a base and solvent combination sufficient to substantially deprotonate the hydroxyimino group of (IV). Furthermore, the oxime anion must be reasonably stable under the reaction conditions for the time period required to complete the isomerization process.

Upon addition of the base to (IV), an equilibrium condition is created as shown in the following equation:

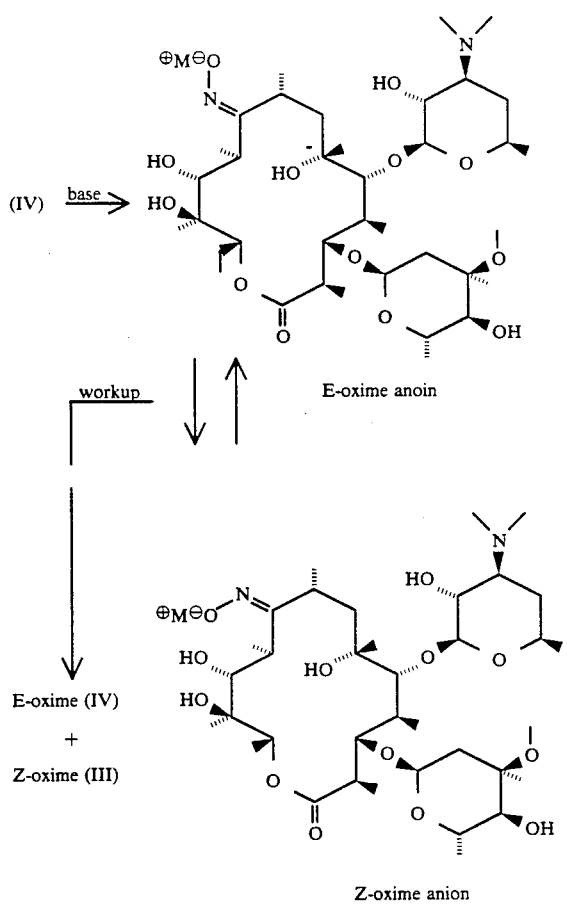

E-oxime anoin (IV) $\xrightarrow{\text{base}}$ workup

E-oxime (IV)
+
Z-oxime (III)

Z-oxime anion where $\oplus M$ is a suitable counterion

The workup performed on the anions includes protonation of the oxime anions to give the neutral oxime product mixture from which the desired Z-isomer is isolated by crystallization or by chromatography followed by crystallization.

The relative amounts of E and Z oxime anions (and neutral oximes after the workup) in the equilibrium mixture can be controlled and depends on a number of factors. These include (a) the strength and quantity of the base reagent, (b) the size and polarizability of the counterion +M, (c) the reaction solvent, and (d) the reaction temperature.

Suitable bases include hydroxides, alkoxides, carbonates, metal amides, amines and metal hydrides.

The following list of reagents is given to illustrate suitable bases and solvents, although the list is not to be taken as exhaustive and other bases and solvents known to those of ordinary skill in the art are not excluded. Preferred bases and solvents are indicated by an asterisk and most preferred bases are indicated by a dagger.

| Bases | | |
|---|---|---|
| 1. Hydroxides | | |
| * | LiOH | lithium hydroxide |
| * | NaOH | sodium hydroxide |
| * | KOH | potassium hydroxide |
|   | CsOH | cesium hydroxide |
|   | Ca(OH)$_2$ | calcium hydroxide |
|   | Mg(OH)$_2$ | magnesium hydroxide |
| * | Me$_4$NOH | tetramethylammonium hydroxide |

-continued

| Bases | | |
|---|---|---|
|   | BnMe$_3$NOH | benzyltrimethylammonium hydroxide |
|   | Et$_4$NOH | tetraethylammonium hydroxide |
|   | Bu$_4$NOH | tetrabutylammonium hydroxide |
| 2. Alkoxides | | |
| * | LiOMe | lithium methoxide |
| * | LiOEt | lithium ethoxide |
|   | LiOiPr | lithium isopropoxide |
|   | LiOnBu | lithium n-butoxide |
|   | LiOsBu | lithium sec-butoxide |
| * | NaOMe | sodium methoxide |
| * | NaOEt | sodium ethoxide |
|   | NaOPr | sodium n-propoxide |
|   | NaOiPr | sodium iso-propoxide |
|   | NaOnBu | sodium n-butoxide |
|   | NaOsBu | sodium sec-butoxide |
|   | NaOtBu | sodium tert-butoxide |
|   | NaOSiMe$_3$ | sodium trimethylsilanoate |
|   | KOMe | potassium methoxide |
| * | KOEt | potassium ethoxide |
|   | KOtBu | potassium tert-butoxide |
|   | KOSiMe$_3$ | potassium trimethylsilanoate |
|   | KOsBu | potassium sec-butoxide |
|   | CsOtBu | cesium tert-butoxide |
|   | Ca(OMe)$_2$ | calcium methoxide |
| * | Mg(OEt)$_2$ | magnesium ethoxide |
|   | Ti(OEt)$_4$ | titanium (IV) ethoxide |
|   | Ti(OiPr)$_4$ | titanium (IV) isopropoxide |
|   | BnMe$_3$NOMe | benzyltrimethylammonium-methoxide |
| 3. Carbonates | | |
|   | K$_2$CO$_3$ | potassium carbonate |
| * | Cs$_2$CO$_3$ | cesium carbonate |
|   | Na$_2$CO$_3$ | sodium carbonate |
| 4. Amides (for use in aprotic solvents) | | |
|   | LiNH$_2$ | lithium amide |
|   | LiNMe$_2$ | lithium dimethylamide |
| * | LiNiPr$_2$ | lithium diisopropylamide |
|   | LiN(C$_6$H$_{11}$)$_2$ | lithium dicyclohexylamide |
|   | LiN(SiMe$_3$)$_2$ | lithium bis(trimethylsilyl) amide |
|   | NaNH$_2$ | sodium amide |
|   | KN(SiMe$_3$)$_2$ | potassium bis(trimethylsilyl) amide |
| 5. Amines | | |
| * | TMG | 1,1,3,3-tetramethyl guanidine |
|   | DBU | 1,8-diazabicyclo[5,4,0]undec-7-ene |
|   | proton sponge | 1,8-bis(dimethylamino)-naphthalene |
| 6. Hydrides (for use in aprotic solvents) | | |
|   | LiH | lithium hydride |
| * | NaH | sodium hydride |
|   | KH | potassium hydride |
| 7. Solvents | | |
| a. | Protic | |
|   | H$_2$O (generally used in combination with an alcohol solvent) | |
| * | MeOH | methanol |
| * | EtOH | ethanol |
| * | iPrOH | isopropanol |
|   | n-BuOH | normal-butanol |
|   | s-BuOH | sec-butanol |
|   | t-BuOH | tert-butanol |
| b. | Aprotic | |
|   | i. Nonpolar (as a group, these are generally used in combination with a protic or polar solvent) | |
|   | Et$_2$O | diethyl ether |
|   | THF | tetrahydrofuran |
|   | DME | dimethoxyethane |
|   | PhMe | toluene |
|   | CH$_2$Cl$_2$ | dichloromethane |
|   | CHCl$_3$ | chloroform |
|   | ii. Polar | |
| * | DMF | dimethylformamide |
|   | DMAC | dimethylacetamide |
|   | DMI | 1,3-dimethyl-2-imidazolidinone |
| * | NEP | 1-ethyl-2-pyrrolidinone |

| Bases | | |
|---|---|---|
| * | NMP | 1-methyl-2-pyrrolidinone |
| | HMPA | hexamethylphosphoramide |
| | $MeNO_2$ | nitromethane |
| * | MeCN | acetonitrile |
| | dioxane | |
| | pyridine | |
| | DMSO | dimethyl sulfoxide |

Preferably, the isomerization reaction is carried out at a concentration of 1–25% w/v of E-oxime to solvent, and most preferably at 10% w/v. The amount of base used is preferably 1.0–10.0 molar equivalents based on the amount of starting E-oxime, more preferably 1.0–3.0 molar equivalents, and most preferably 2.0 molar equivalents. The reaction is generally run at a temperature of from 0° C. to 80° C., and more preferably at 22°–25° C. The reaction can be allowed to run for 0.5 hour to 20 days, but most preferably is carried out over 20–24 hours.

Beckmann Rearrangement of
(9Z)-9Deoxo-9-hydroxyiminoerythyomycin A rangement involves initial conversion of the oxime hydroxyl group to a leaving group which is then lost with concomitant migration of the oxime carbon substituent that is situated anti to the leaving group. In aqueous media, the intermediate nitrilium cation thus formed usually reacts with water to afford the amide product. The nitrilium intermediate can also be trapped by other suitable nucleophiles thereby leading to imino products such as imidates and amidines.

The Beckmann rearrangement has been accomplished under a variety of acidic, neutral and basic conditions. Common acidic reagents that promote the transformation include concentrated sulfuric acid, polyphosphoric acid, thionyl chloride, phosphorous pentachloride, sulfur dioxide, and formic acid. These reagents are generally not applicable to the rearrangement of oxime (III) due to the sensitivity of the macrolide molecule, and especially the cladinose sugar residue, to acidic conditions. Efficient Beckmann rearrangement also occurs by heating the oxime with silica gel in xylene or under mildly basic conditions by heating the oxime in hexamethylphosphoramide. These conditions are not particularly valuable for the conversion of (III) to products (V), (VI) and (VII) due to competing isomerization of the oxime function under the reaction conditions.

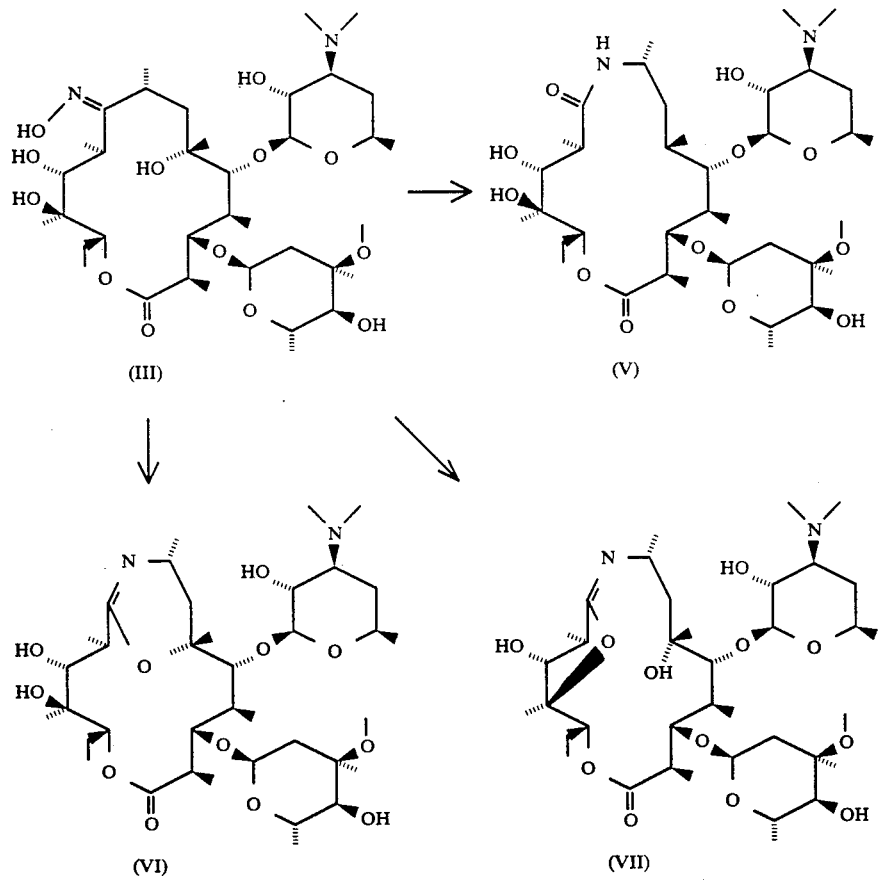

The conversion of (9Z)-9-deoxo-9-hydroxyiminoerythromycin A (III) to the 8a-aza-8a-homoerythromycin products (V), (VI) and (VII) is accomplished by means of the Beckmann rearrangement (see "Comprehensive Organic Chemistry", I. O. Sutherland (Ed.), Pergamon Press, New York, 1979, Vol. 2, pgs. 398–400 and 967–968). In general, the Beckmann rearrangement of ketoximes leads to carboxamides and, in cyclic systems, to ring expanded lactams, The mechanism of the rear- A preferred method for effecting the Beckmann rearrangement involves initial O-sulfonylation of the oxime group with an alkylsulfonyl halide, arylsulfonyl halide or arylsulfonic anhydride. The intermediate oxime sulfonate thus formed can be isolated or, as more commonly practiced, converted in situ to the rearranged products. The sulfonylation and rearrangement reactions are generally performed in the presence of an organic or inorganic base. This method is particularly valuable for the conversion of oxime (III) to the rearranged products (V), (VI), and (VII).

Preferred sulfonylating reagents for effecting the rearrangement of oxime (III) include methanesulfonyl chloride, benzenesulfonyl chloride, 4-acetamidobenzenesulfonyl chloride, p-toluenesulfonyl chloride, benzenesulfonic anhydride, and p-toluenesulfonic anhydride. The reaction is carried out in the presence of an inorganic base such as sodium bicarbonate or potassium carbonate, or in the presence of an organic base such as pyridine, 4-dimethylaminopyridine, triethylamine, or N,N-disopropylethylamine. Suitable solvents include aqueous mixtures such as aqueous acetone or aqueous dioxane and organic solvents such as dichloromethane, chloroform, ethyl acetate, diethyl ether, tetrahydrofuran, toluene, acetonitrile, and pyridine. Mixtures of organic solvents, especially those containing pyridine, are highly useful. The reaction is generally performed using 1-3 molar equivalents of the sulfonylating agent and one or more molar equivalents of base at a reaction temperature of $-20°$ C. to $50°$ C. Pyridine is often used as both solvent and base.

The distribution of products resulting from Beckmann rearrangement of oxime (III) depends on the particular reaction conditions employed. For example, when the rearrangement is effected with p-toluenesulfonyl chloride and sodium bicarbonate in aqueous acetone, the major products are the lactam (V) and the 6,9-bridged iminoether (VI). When the reaction is conducted under anhydrous conditions such as p-toluenesulfonyl chloride in pyridine, the major products are the 6,9-bridged and 9,12-bridged iminoethers (VI) and (VII). The ratio of products (VI) and (VII) is also effected by the addition of co-solvents, by temperature, and by the initial oxime concentration. In general, increasing the proportion of pyridine as solvent, increasing the reaction temperature, and decreasing the initial oxime concentration all favor the formation of the 9,12-product (VII) over that of the 6,9-product (VI).

A particularly preferred method for effecting the Beckmann rearrangement of oxime (III) involves the addition of a solution of 2.5 molar equivalents of p-toluenesulfonyl chloride in diethyl ether to a solution of the oxime in pyridine at $0°-5°$ C. Oxime O-sulfonylation and subsequent rearrangement occur under the reaction conditions to afford a 1:3 mixture of iminoether products (VI) and (VII).

The products of the Beckmann rearrangement of oxime (III) are conveniently purified by chromatographic methods. For example, the lactam (V) is easily separated from iminoether (Vi) using column chromatography on silica gel or by reverse phase, high-pressure liquid chromatography. Products (VI) and (VII) can also be separated by chromatographic methods, and the (VII) thus obtained can be further purified by crystallization. If the cyclic iminoethers are to be processed further, it is generally expedient to simply carry the mixture of (VI) and (VII) isomers into the subsequent reduction step without further purification.

As previously noted, Beckmann rearrangement of oxime (III) under anhydrous conditions leads to a product mixture comprised of the 6,9- and 9,12-bridged iminoethers (VI) and (VII). The 9,12-bridged product, which is formed by internal trapping of the intermediate nitrilium species by the hydroxyl group at C-12, is initially isolated as a mixture of major and minor forms that are isomeric about the imino double bond. The initial mixture of isomers equilibrates at room temperature, both in solution or on storing as a crude foam, to approximately a 1:1 mixture of isomers. The first-formed, major isomer can be isolated from the mixture by crystallization from nitromethane solution. However, it should be noted that the equilibration of the 9,12-bridged iminoethers (VII) is of no consequence to the overall process since both forms are easily reduced in the next step to 9-deoxo-8a-aza-8a-homoerythromycin A.

Reduction of
9Deoxo-6deoxy-6,9eopxy-8a,9-didehydro-8a-aza-8a-homoerythromycin A (VI) and
9-Deoxo-12-deoxy-9,12-epoxy-8a,9-didehydro-8a-aza-8a-homoerythromycin A (VII)

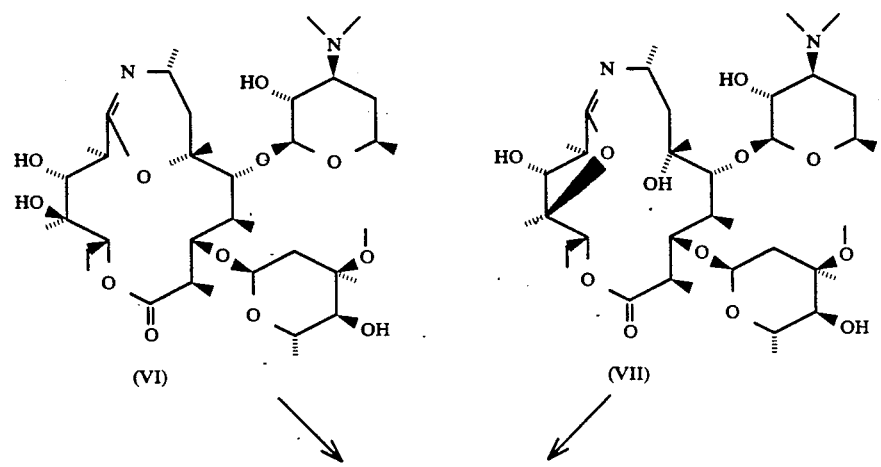

(VI)   (VII)

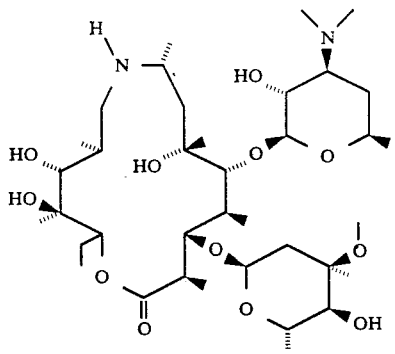

(VIII)

Compounds (VI) and (VII) can be viewed as cyclic imidates (or imidic acid esters) of the macrocyclic lactam (V). The imidates are formally derived from compound (V) by transannular addition of the hydroxy groups at positions 6 and 12 to the lactam carbonyl group, followed by elimination of water. Imidates (VI) and (VII) most likely arise by intramolecular interception of the Beckmann rearrangement nitrilium intermediate with the 6- and 12- hydroxy group. In structure (VI), the imidate function (—N=C—O—) lies completely with a 6-membered ring thereby giving rise to a 5,6-dihydro-1,3-oxazine system. By contrast, the second structure (VII) has the imino nitrogen atom exocyclic to a 5-membered ring containing the oxygen atom thereby giving rise to a 2-iminotetrahydrofuran system.

A number of reagents are known for the reduction of imidates to the corresponding amines (see "The Chemistry of Amidines and Imidates", S. Patai (Ed.), John Wiley and Sons, 1975, pgs. 460–461 and "Comprehensive Organic Chemistry", I. O. Sutherland (Ed.), Pergamon Press, New York, 1979, Vol. 2, pg. 495). These include metal/proton-donor combinations such as sodium amalgam in acid solution or sodium in ethanol or liquid ammonia, catalytic hydrogenation under pressure, and complex metal hydrides such as lithium aluminum hydride and sodium borohydride. The electrochemical reduction of imidates is also reported to give amines in good yield.

A method of choice for reducing the macrocyclic imidates (VI) and (VII) to the amine (VIII) uses a complex metal hydride in an appropriate solvent system. Suitable hydride reagents include lithium aluminum hydride, sodium borohydride, sodium cyanoborohydride, and diisobutyl aluminum hydride. Both lithium aluminum hydride and diisobutyl aluminum require the use of anhydrous solvents such as benzene, toluene, diethyl ether, tetrahydrofuran and dimethoxyethane, whereas sodium borohydride and sodium cyanoborohydride can be used in the presence of water or in alcoholic solvents such as methanol, ethanol, isopropanol, and ethylene glycol. When sodium cyanoborohydride is used the reaction medium is usually acidified by addition of aqueous acid (pH ≧3) or acetic acid. The reaction is generally accomplished by treating the imidate with 1–5 molar equivalents of reductant for 1–20 hours at a temperature ranging from −20° C. to 50° C.

A particularly preferred method for reducing imidates (VI) and (VII) to the amine (VIII) employs 2–3 molar equivalents of sodium borohydride in methanol or ethylene glycol at a temperature of 0° C. to 25° C. Ethylene glycol serves the dual purposes of activating the borohydride agent and of breaking up borate ester complexes of the amine product.

A second method of choice for effecting the reduction of imidates (VI) and (VII) to the amine (VIII) is catalytic hydrogenation at high pressure. The reaction is usually accomplished by shaking a mixture of imidate and catalyst in a suitable solvent such as methanol, ethanol, aqueous dioxane or acetic acid at a hydrogen pressure of 1000–3000 psi for 2–20 hours at ambient temperature. Suitable catalysts include noble metals and their oxidized forms such as platinum oxide (Adams' catalyst), palladium on carbon, palladium hydroxide on carbon (Pearlman's catalyst) and rhodium on carbon. An especially preferred method for reducing imidate (VI) uses nearly an equivalent weight of platinum oxide catalyst in acetic acid at 2000 psi hydrogen for 18–20 hours at room temperature.

Methylation of 9-Deoxo-8a-aza-8a-homoerythromycin A

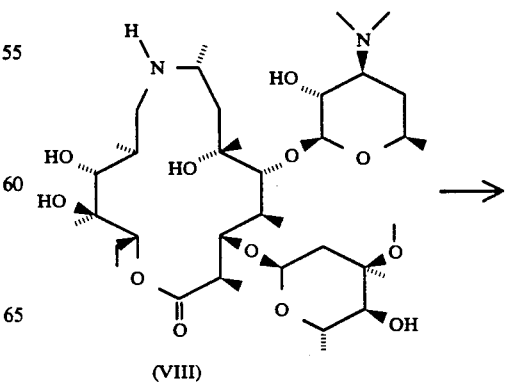

(VIII)

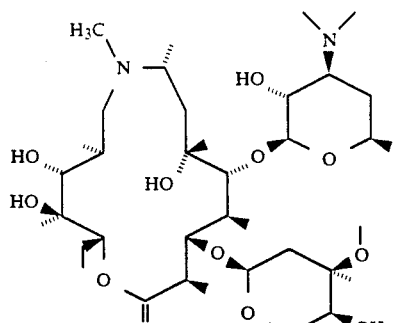

(IX)

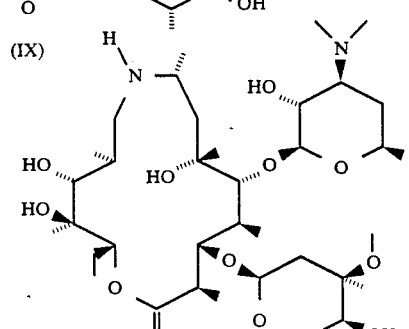

(VIII)

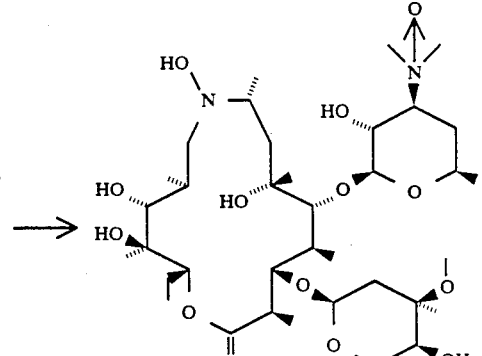

(X)

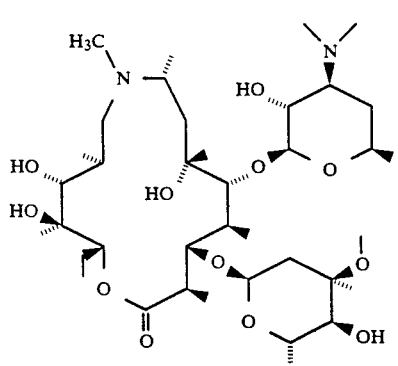

(IX)

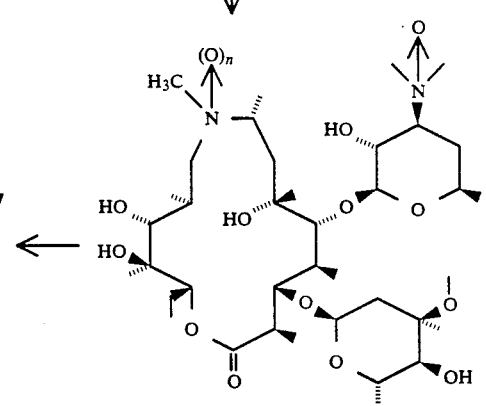

(XI)

n = 0 or 1

Secondary amines such as (VIII) can be reductively methylated to tertiary amines using formaldehyde in the presence of a reducing agent. Suitable reductants for this reaction include hydrogen in the presence of a noble metal catalyst, Raney nickel, sodium borohydride, sodium cyanoborohydride, and formic acid. The reaction can be conducted in a number of organic solvents, for example methanol, ethanol, acetonitrile, chloroform, tetrahydrofuran or dioxane, with or without the presence of added water. Perhaps the most common of these methylation procedures is the Eschweiler-Clarke method, which involves the reaction of the amine with formaldehyde in the presence of formic acid.

Application of the Eschweiler-Clarke procedure to compound (VIII) affords the ring methylated product (IS). The reaction is accomplished by treating (VIII) with 1-2 molar equivalents of formaldehyde and 2-3 molar equivalents of formic acid in an inert solvent at 20°-100 ° C. A preferred system uses 37% aqueous formaldehyde and formic acid in carbon tetrachloride or chloroform heated at reflux for 1-2 days. The product is conveniently isolated by crystallization from aqueous ethanol.

The methylation of compound (VIII) can also be accomplished using a three-step procedure (see G. M. Bright, et al., J. Antibiotics, 41, 1029 (1988) and U.S. Pat. No. 4,474,768) in which (VIII) is first oxidized to the N-hydroxide N'-oxide intermediate (X), then treated with a methylating agent to afford the intermediate product (XI), and finally deoxygenated to the desired product. In this approach, the N'-oxygen serves as a temporary protecting group to prevent quaternization at the desosamine dimethylamino group.

The oxidation step is conducted in an inert solvent using hydrogen peroxide or a peracid such as peracetic acid or 3-chloroperoxybenzoic acid as the oxidant. Suitable solvents for the reaction include dichloromethane, chloroform, tetrahydrofuran, dioxane, methanol, ethanol and acetic acid. In general, a water miscible solvent such as methanol or acetic acid is used with the water-soluble oxidants hydrogen peroxide and peracetic acid, whereas an anhydrous solvent such as dichloromethane or tetrahydrofuran is used with 3-chloroperoxybenzoic acid. The reaction is usually accomplished with an excess of oxidant (2–40 molar equivalents) at a temperature of from 0° C. to 50° C. for up to 24 hours. A particularly preferred embodiment employs excess 30% aqueous hydrogen peroxide as oxidant in methanol solvent at room temperature for 18–20 hours.

Introduction of the ring N-methyl group is accomplished by treating the N-hydroxy-N'-oxide intermediate (X) with a methylating agent in an inert solvent in the presence of an acid acceptor. An inert solvent is defined as one that will not react with the methylating reagent under the reaction conditions. Suitable solvents include but are not limited to dichloromethane, chloroform, tetrahydrofuran, dimethyoxyethane, dimethylsulfoxide, and toluene. Of the numerous methylating agents that are known to effect alkylation at nitrogen, methyl iodide, methyl bromide, dimethyl sulfate and methyl trifluoromethanesulfonate are well suited for the present application. The acid acceptor component, which serves to neutralize the acid formed on reaction of the methylating agent with the ring nitrogen atom, can be an inorganic base such as an alkali metal hydroxide or carbonate, or a hindered amine base. Examples, of suitable acid acceptors are sodium bicarbonate, potassium carbonate, potassium hydroxide, and 2,6-lutidine. The methylation reaction is generally accomplished using a large excess (10–75 molar equivalents) of both the methylating agent and the acid acceptor at a temperature of from 0° C.–80° C. for 1–20 hours. A preferred method involves stirring compound (X) with approximately 40 molar equivalents of methyl iodide and 70 molar equivalents of anhydrous potassium carbonate in dichloromethane at room temperature. The product of the methylation reaction is usually obtained as a mixture of components (Xi, n=0 and 1) wherein the ring nitrogen atom has suffered partial deoxygenation. These components can be separated by chromatography, but are generally used without purification in the following deoxygenation step.

The final step of the sequence, the deoxygenation reaction of (XI) to provide (IX), is readily accomplished by catalytic hydrogenation. The hydrogenation reaction is carried out at a temperature of 18° C. to 25° C. and at hydrogen pressures of from 15 psi to 2000 psi in an inert solvent. Suitable catalysts are noble metals and their oxides such as palladium on carbon, palladium hydroxide on carbon, platinum oxide, platinum on carbon, and rhodium on carbon. Representative inert solvents for the catalytic reduction are methanol, ethanol, tetrahydrofuran, dioxane, acetic acid and mixtures thereof. A typical catalytic reduction procedure uses ethanol as solvent, a hydrogen pressure or 45 psi, and 10% palladium on carbon as catalyst at a substrate to catalyst ratio of 1:1 to 1:2.

The reductive deoxygenation of (XI) to (IX) can also be accomplished with a number of chemical reductants. Representative reagents of this type include metal hydrides such as sodium borohydride or sodium cyanoborohydride, zinc in acetic acid, and triphenylphosphine.

As antibiotics, the compounds of formula (II) can be administered in such oral dosage forms as tablets, capsules, pills, powders, granules, elixirs, tinctures, suspensions, syrups and emulsions. Likewise, they may also be administered in intravenous, intraperitoneal, subcutaneous or intramuscular form, all using forms well known to those of ordinary skill in the pharmaceutical arts. In general, the preferred form of administration is oral. An effective but non-toxic amount of the compound can be employed as a mammalian antibiotic.

The dosage regimen utilizing the compounds of formula (II) is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Dosages of the compounds of formula (II), when used for the indicated effects, will range between about 0.2 mg per kg of body weight per day (mg/kg/day) to about 120 mg/kg/day and preferably 4–50 mg/kg/day. Advantageously, the compound may be administered in a single daily dose, or the total daily dosage may be administered in divided doses of two, three or four times daily.

Furthermore, the compounds of formula (II) can be administered in topical, otic or opthalmic form via use of suitable vehicles.

In the methods of using the compounds (II), they can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups, and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol, and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Disintegrators include, without limitation, starch, methyl cellulose, agar, bentonite, xanthan gum, and the like.

The compounds of formula (II) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (II) may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the compound of formula (II) may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The following examples further illustrate details for the practice of the invention. Those skilled in the art will readily understand that known variations, when taken with the alternative bases and solvents taught above, can be used in the synthesis of the invention.

EXAMPLE 1

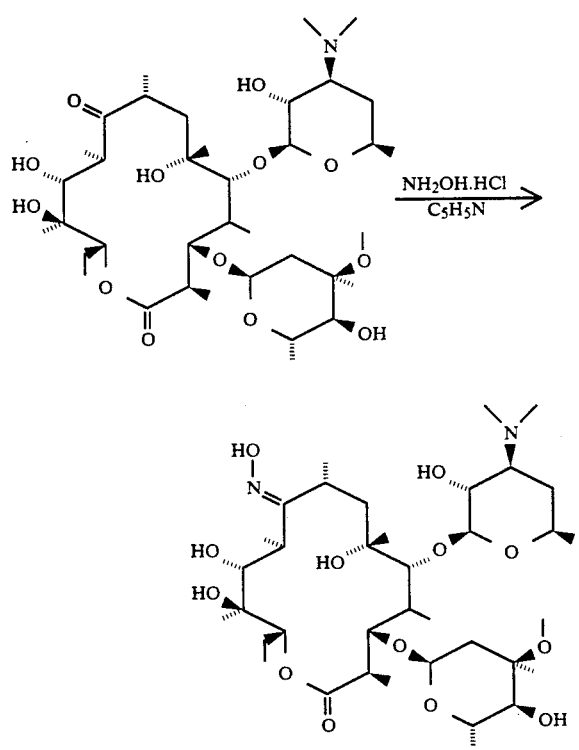

Preparation of
(9E)-9-Deoxo-9-hydroxyiminoerythromycin A

Hydroxylamine hydrochloride (224 g, 3.23 mol) was added to a solution of erythromycin A (100 g, ca. 95% pure, 0.129 mol, available from Aldrich Chemical, Inc., Milwaukee, Wisconsin) in pyridine (500 mL). The resulting mixture was stirred at room temperature for 27 ours, and then concentrated under vacuum at ca. 40° C. The semi-solid residue was kept under high vacuum overnight, then stirred with ethanol (600 mL) for 15 minutes and filtered. The collected solids were washed with hot (50° C.) ethanol. The combined filtrate and washing was evaporated under vacuum to a pale blue foam. The foam was shaken with water (850 mL) to give a thick emulsion which was stirred rapidly at room temperature for 2.5 hours to give a filterable precipitate. The precipitate was collected, washed with water (150 mL), and dried under vacuum to give a white solid (117.7 g).

The crude oxime hydrochloride was suspended in 5% aqueous sodium bicarbonate (1000 mL) and methylene chloride (1000 mL), and the mixture was stirred while the pH was adjusted to 9.5 by addition of 5N aqueous sodium hydroxide. The layers were separated and the aqueous portion was extracted with ethyl acetate (500 mL) and ethyl ether (500 mL). The combined organic layer and extracts were dried over sodium sulfate, filtered, and evaporated under vacuum to a white solid (92.3 g). The solid was dissolved in hot ethyl acetate (250 mL), and the solution diluted with hot hexanes (400 mL) and left overnight in a refrigerator. The crystals of 9-deoxo-9(E)-hydroxyiminoerythromycin A were collected, washed with ice-cold hexane (250 mL), and dried under vacuum to afford a white solid (88.5 g).

IR (CH$_2$Cl$_2$) 3560, 3400 (br), 2980, 2950, 1735, 1460, 1389, 1165, 1110, 1085, 1050, and 1010 cm$^{-1}$.

$^1$H NMR (CDCl$_3$) δ 5.05 (dd, H—13), 4.90 (d, H—1″), 4.38 (d, H—1′), 4.01 (m, H—5″), 3.99 (d, H—3), 3.74 (m, H—8), 3.66 (s, H—11), 3.54 (d, H—5), 3.45 (m, H—5′), 3.28 (s, OCH$_3$), 3.23 (dd, H—2′), 2.96 (t, H—4″), 2.87 (m, H—2), 2.64 (q, H—10), 2.43 (m, H—3′), 2.32 (d, H—2″ eq), 2.27 (s, N(CH$_3$)$_2$), 1.98 (m, H—4), 1.87 (m, H—14a), 1.63 (m, H—4′ eq), and 1.46 (s, 6—CH$_3$).

$^1$H NMR (CD$_3$OD) δ 5.19 (dd, H—13), 4.48 (d, H—1′), 4.15 (dq, H—5″), 3.98 (d, H—3), 3.76 (m, H—8), 3.70 (m, H—5′), 3.67 (s, H—11), 3.58 (d, H—5), 3.33 (s, OCH$_3$), 3.23 (dd, H—2′), 3.01 (d, H—4″), 2.92 (m, H—2), 2.72 (m, H—10), 2.70 (m, H—3′), 2.43 (d, H—2′-'eq), 2.33 (s, N(CH$_3$)$_2$), 2.01 (m, H—4), 1.88 (m, H—14a), 1.72 (m, H—4′eq), 1.58 (dd, H—2″b), 1.48 (m, H—14ax), 1.45 (s, 6—CH$_3$), 1.26 (d, 5″—CH$_3$), 1.23 (s, 3″—CH$_3$), 1.14 (s, 12—CH$_3$), 1.10 (d, 4—CH$_3$), 1.05 (d, 8—CH$_3$), and 0.84 (t, CH$_2$CH$_3$).

$^{13}$C NMR (CDCl$_3$) δ 175.3, 171.3, 103.1, 96.3, 83.5, 80.3, 78.1, 77.1, 75.1, 74.3, 72.6, 71.2, 70.9, 68.8, 65.4, 65.3, 49.4, 44.6, 40.3, 38.8, 37.8, 35.1, 32.6, 29.2, 27.0, 25.4, 21.5, 21.3, 18.7, 18.6, 17.3, 14.3, 10.6, and 9.3.

$^{13}$C NMR (CD$_3$OD) δ 177.5, 171.6, 104.0, 98.0, 84.1, 81.2, 79.3, 78.3, 76.3, 74.2, 72.9, 72.2, 69.0, 66.8, 65.2, 50.0, 46.3, 40.7, 39.3, 36.2, 32.0, 27.4, 26.7, 22.3, 22.0, 21.6, 19.3, 19.1, 17.3, 16.6, 14.8, 11.2, and 10.2.

EI Mass Spectrum, m/e 748, 590, 462, 431, 416, 398, 174, 159, 158, and 116.

EXAMPLE 2

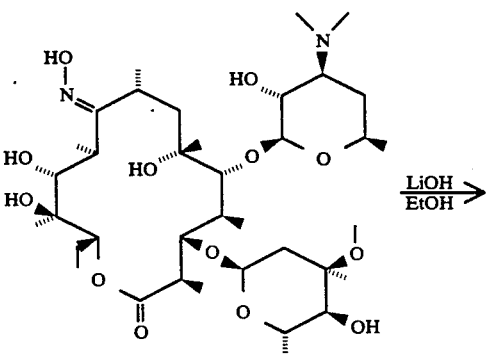

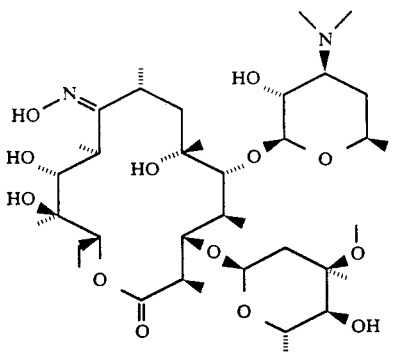

Conversion of (9E)-9-Deoxo-9-hydroxyiminoerythromycin A to (9Z)-9-hydroximinoerythromycin A

Method 1

(9E)-9-Deoxo-9-hydroxyiminoerythromycin A (20.0 g, 26.7 mMol) was added to a stirred solution of lithium hydroxide monohydrate (2.25 g, 53.5 mMol) in absolute ethanol (200 mL). The solution was blanketed with nitrogen and stirred overnight at room temperature. The solvents were evaporated under vacuum and the residue was partitioned between ethyl acetate (200 mL) and brine (120 mL). The pH of the mixture was adjusted from 11 to 9.3 with 2N hydrochloric acid. The ethyl acetate was removed and the brine was re-extracted with more ethyl acetate (2×200 mL). The combined ethyl acetate extracts were washed with brine (100 mL), dried with anhydrous magnesium sulfate, filtered and evaporated under vacuum to a foam (ca. 20 g).

The crude oxime mixture was dissolved in methylene chloride (220 mL) and stirred for 1 hour at room temperature to give a filterable, white solid (18.7 g). This material was dissolved in ethyl acetate (100 mL), diluted with nitromethane (100 mL), and 50 mL of solvent was evaporated under vacuum. Additional nitromethane (50 mL) was added and 80 mL of solvent was evaporated under vacuum. The solution was seeded with the (9Z)-isomer and stirred at room temperature for 3 hours. The resulting suspension was filtered and the solids were rinsed with nitromethane (20 mL) and dried under a stream of nitrogen to afford 9-deoxo-(9Z)-hydroxyiminoerythromycin A (14.8 g, 74% yield) as a white solid.

MP 147°-164° C.

IR (CHCl$_3$) 3680, 3435 (br), 2970, 2940, 1725, 1455, 1375, 1345, 1165, 1105, 1085, 1045, 1005, and 950 cm$^{-1}$.

$^1$H NMR (CDCl$_3$) δ 5.01 (dd, H—13), 4.87 (d, H—1″), 4.40 (d, H—1′), 3.98 (m, H—3 and H—5″), 3.80 (s, H—11), 3.49 (m, H—5 and H—5′), 3.27 (s, OCH$_3$), 3.21 (dd, H—2′), 2.99 (m, H—4″), 2.8 m, H—8, H—2 and H—10), 2.74 (m, H—10), 2.43 (m, H—3′), 2.32 (d, H—2″eq), 2.27 (s, N(CH$_3$)$_2$), 1.91 (m, H—4), 1.87 (m, H—14a), 1.63 (m, H—4′eq), 1.51 (m, H—2″b and H—7), 1.42 (m, H—14ax), 1.37 (s, 6—CH$_3$), 1.28 (d, 10—CH$_3$), 1.24 (d, 5″—CH$_3$), 1.19 (s, 3″—CH$_3$), 1.18 (d, 5′—CH$_3$), 1.12 (d, 2—CH$_3$), 1.11 (s, 12—CH$_3$), 1.08 (d, 8—CH$_3$), 1.04 (d, 4—CH$_3$), and 0.79 (t, CH$_2$CH$_3$).

$^1$H NMR (CD$_3$OD) δ 5.20 (br d, H—13), 4.50 (br d, H—1′), 4.16 (dq, H—5″), 4.02 (d, H—3), 3.70 (m, H—5′), 3.56 (br d, H—5), 3.34 (s, OCH$_3$), 3.25 (dd, H—2′), 3.03 (d, H—4″), 2.87 (m, H—8), 2.84 (m, H—2), 2.73 (m, H—3′), 2.44 (d, H—2″eq), 2.33 (s, N(CH$_3$)$_2$), 1.97 (m, H—4), 1.88 (m, H—14a), 1.73 (m, H—4′eq), 1.64 (m, H—7), 1.59 (dd, H—2″b), 1.47 (m, H—14ax), 1.36 (br s, 6—CH$_3$), 1.28 (d, 5″—CH$_3$), 1.24 (s, 3″—CH$_3$), 1.18 (m, 5′—CH$_3$, 2—CH$_3$, 8—CH$_3$ and 10—CH$_3$)), 1.13 (s, 12—CH$_3$), 1.08 (d, 4—CH$_3$), and 0.86 (t, CH$_2$CH$_3$).

$^{13}$C NMR (CDCl$_3$) δ 176.2, 168.2, 102.8, 95.9, 83.6 (br), 79.3 (br), 77.9, 77.3, 75.2, 75.1, 72.7, 71.0, 70.9, 68.8, 65.5, 65.3, 49.4, 40.2, 39.9 (br), 37.8 (br), 35.7 (br), 34.9, 34.1 (br), 28.9, 26.0 (br), 21.4, 21.3, 19.8 (br), 18.4, 16.8, 15.3 (br), 10.7, and 9.2.

$^{13}$C NMR (CD$_3$OD) δ 177.7, 170.0, 103.9, 97.7, 84.3 (br), 80.7, 79.2, 78.1, 77.0 (br), 76.1, 74.1, 72.8, 71.7 (br), 69.2, 66.7, 65.1, 49.9, 46.2 (br), 41.8 (br), 40.8, 40.5 (br), 36.0, 33.8 (br), 31.9, 26.7 (br), 22.8, 21.8, 21.7 (br), 21.6, 19.1, 17.5, 15.8 (br), 12.2 (br), 11.3, and 10.1.

FAB mass spectrum, m/e 749, 591, 416, 398, 174, 159, 158, and 116.

Elemental Analysis.

Calculated for C$_{37}$H$_{68}$N$_2$O$_{13}$: C, 59.34; H, 9.15; N, 3.74.

Found: C, 59.12; H, 8.80; N, 3.82.

Method 2: 1.0 LiOH in EtOH (9E)-9-Deoxo-9-hydroxyiminoerythromycin A (255 mg, 0.34 mmol) was added to a solution of lithium hydroxide monohydrate (14.3 mg, 0.34 mmol) in absolute ethanol (2.55 mL). The resulting solution was stirred at room temperature for 25 hours, and then stored in a freezer at −20° C. for 68 hours. After warming to room temperature, the solution was evaporated under reduced pressure to remove the solvent. The residue was stirred with saturated aqueous sodium chloride (5 mL) and ethyl acetate (5 mL) while the pH was adjusted to 9.2 by addition of dilute hydrochloric acid. After shaking, the phases were separated and the aqueous portion extracted with more ethyl acetate (2×2.5 mL). The combined ethyl acetate extracts were washed with saturated sodium chloride solution (4 mL), dried over magnesium sulfate, filtered and evaporated at reduced pressure to afford a white foam (263 mg). Examination of this material by $^1$H NMR spectroscopy revealed a 31:69 mixture of (9E)-9-deoxo-9-hydroxyiminoerythromycin A and (9Z)-9-deoxo-9-hydroxyiminoerythromycin A.

Method 3: 2.0 LiOH in EtOH (9E)-9-Deoxo-9-hydroxyiminoerythromycin A (291 mg, 0.333 mmol) was added to a solution of lithium hydroxide monohydrate (32.6 mg, 0.776 mmol) in absolute ethanol (2.9 mL). The resulting solution was stirred at room temperature and under a nitrogen atmosphere for 22.5 hours. The solvent was evaporated at reduced pressure the residue stirred with ethyl acetate (5 mL) and saturated aqueous sodium chloride (5 mL) while adjusting the pH to 9 by addition of 2N hydrochloric acid. The mixture was shaken, the phases separated, and the aqueous portion extracted with more ethyl acetate (2×2.5 mL). The combined ethyl acetate extracts were washed with saturated sodium chloride solution (4 mL), dried with magnesium sulfate, filtered and evaporated under vacuum to a white foam (299 mg). This material was shown by $^1$H NMR to be a 21:79 mixture of (9E)-9-deoxo-9-hydroxyiminoerythromycin A and (9Z)-9-deoxo-9-hydroxyiminoerythromycin A.

Method 4: 3.0 LiOH in EtOH (9E)-9-Deoxo-hydroxyiminoerythromycin A (239 mg, 0.319 mmol) was was added to a mixture of lithium hydroxide monohydrate (40.2 mg, 0.957 mmol) in absolute ethanol (2.4 mL), and the resulting solution was stirred at room temperature under a nitrogen atmosphere for 21.7 hours. Workup as described in method 3 afforded a white foam (236 mg) shown by $^1$H NMR to consist of a 19.81 mixture of (9E)-9-deoxo-hydroxyiminoerythromycin A and (9Z)-9-deoxo-hydroxyiminoerythromycin A.

Method 5: 2.0 NaOEt in EtOH

Freshly cut sodium metal (48 mg, 2.087 mmol) was dissolved in absolute ethanol (7.8 mL) under a nitrogen atmosphere. (9E)-9-Deoxo-hydroxyiminoerythromycin A (782 mg, 1.043 mmol) was added and the resulting solution was stirred at room temperature. A crystalline precipitate, identified as the starting oxime by thin layer chromatography, appeared after a few hours. After stirring overnight, the mixture was once again a clear solution. After 54 hours, approximately half (3.9 mL) of the reaction mixture was removed and evaporated under reduced pressure. The gummy residue was stirred with ethyl acetate (5 mL) and saturated aqueous sodium chloride (5 mL) while the pH was adjusted to 9.2 by addition of dilute hydrochloric acid (2N and 0.2N solutions). The mixture was shaken, the layers separated, and the aqueous portion extracted with more ethyl acetate (2×2.5 mL). The combined ethyl acetate solution was washed with brine (5 mL), dried with magnesium sulfate, filtered and evaporated under reduced pressure to a white foam (361 mg). This material was shown by $^1$H NMR spectroscopy to consist of a 22:78 mixture of the (9E) and (9Z) isomers of 9-deoxo-9-hydroxyiminoerythromycin A.

Method 6: 2.0 NaOH in EtOH

The remaining half of the reaction mixture from method 5 was treated with water (0.0188 mL, 1.04 mmol) to give a solution effectively consisting of sodium hydroxide and oxime in ethanol. The solution was stirred at room temperature for 23 hours, then worked up as described in method 5 to give a white foam (402 mg). This material was shown by $^1$H NMR to consist of a 24:76 mixture of the (9E) and (9Z) isomers of 9-deoxo-9-hydroxyiminoerythromycin A.

Method 7: 2.0 LiOH in MeOH

A solution of lithium hydroxide monohydrate (37 mg, 0.88 mmol), (9E)-9-deoxo-9-hydroxyiminoerythromycin A (330 mg, 0.44 mmol), and methanol (3.3 mL) was stirred at room temperature of 65.5 hours. The solution was then stored at −20° C. for 13 days before warming to room temperature and evaporating the solvent at reduced pressure. The residue was stirred with ethyl acetate (5 mL) and brine (5 mL) while adjusting the pH to 9.2 by addition of dilute hydrochloric acid. The mixture was shaken, the layers separated and the aqueous portion extracted with more ethyl acetate (2×2.5 mL). The combined ethyl acetate solution was washed with brine (5 mL), dried with magnesium sulfate, and evaporated under vacuum to provide a white foam (324 mg). NMR analysis of this material indicated a 45:55 ratio of (9E) to (9Z) 9-deoxo-9-hydroxyiminoerythromycin A products.

Method 8: 2.0 NaOMe in MeOH

A solution of (9E)-9-deoxo-9-hydroxyiminoerythromycin A (375 mg, 0.5 mmol) in anhydrous methanol (3.5 mL) was cooled in an ice bath and stirred under a nitrogen atmosphere while methanolic sodium methoxide (0.23 mL of a 25 wt % solution, 1.01 mmol) was added by syringe. The cooling bath was removed and the solution was stirred at room temperature under a nitrogen atmosphere for 66 hours. The solution was then stored at −20° C. for 13.3 days before being processed to a white foam (329 mg) as described in method 7. The product consisted of a 35:65 mixture of (9E)-9-deoxo-9-hydroxyiminoerythromycin A and (9Z)-9-deoxo-9-hydroxyiminoerythromycin A as determined by $^1$H NMR spectroscopy.

Method 9: 10.0 NaOMe in MeOH

A solution of (9E)-9-deoxo-9-hydroxyiminoerythromycin A (100 mg, 0.134 mmol) in anhydrous methanol (4.70 mL) was treated with sodium methoxide (0.305 mL of a 25 wt. % solution in methanol, 1.335 mmol) and stirred at room temperature of 74.5 hours. The solvent was evaporated under reduced pressure and the residue stirred with ethyl acetate (5 mL) and saturated brine (5 mL) while adjusting the pH of the aqueous layer to 9.4 with 9N hydrochloric acid. The mixture was shaken, the layers separated and the aqueous portion extracted with more ethyl acetate (2×2.5 mL). The combined ethyl acetate solution was washed with brine (5 mL), dried with magnesium sulfate, filtered and evaporated at reduced pressure to afford a white foam (102 mg). This material was shown by $^1$H NMR spectroscopy to consist of a 26:74 mixture of the (9E) and (9Z) isomers of 9-deoxo-9-hydroxyiminoerythromycin A.

Method 10: 2.0 LiOH in iPrOH (9E)-9-deoxo-9-hydroxyiminoerythromycin A (279 mg, 0.361 mmol) was added to a partial solution of lithium hydroxide monohydrate (30.3 mg, 0.721 mmol) in isopropanol (2.7 mL), and the mixture was stirred at room temperature in a capped flask. A fine white precipitate ;formed in a few minutes and, after stirring overnight, the mixture was a hazy suspension. After 21 hours, the mixture was transferred to a freezer at −20° C. and stored there for 15 days. After warming to room temperature, the solvent was evaporated under vacuum and the residue stirred with ethyl acetate (5 mL) and brine (5 mL) while adjusting the pH to 9.2 with dilute hydrochloric acid. The mixture was shaken, the layers separated, and the aqueous phase extracted with more ethyl acetate (2×2.5 ml). The combined ethyl acetate solution was washed with brine (4 mL), dried with magnesium sulfate, filtered and evaporated under vacuum to afford a white foam (249 mg). The product consisted of a 26:74 mixture of (9E)-9-deoxo-9-hydroxyiminoerythromycin A and (9Z)-9-deoxo-9-hydroxyiminoerythromycin A as determined by $^1$H NMR spectroscopy.

Method 11: 1.0 LiOH in MeCN

A mixture of (9E)-9-deoxo-9-hydroxyiminoerythromycin A (500 mg, 0.668 mmol), lithium hydroxide monohydrate (28 mg, 0.668 mmol), and absolute ethanol (5 mL) was stirred at room temperature for 10 minutes to give a solution. The solution was evaporated under reduced pressure to afford a residue that was twice diluted with ethanol (10 mL) and evaporated at reduced pressure and then suspended in anhydrous acetonitrile (5 mL) and evaporated at reduced pressure. The solid residue was suspended in anhydrous acetonitrile (5 mL) and the mixture was stirred at room temperature for 18 days. The solvent was evaporated under reduced pressure and the residue was stirred with ethyl acetate (5 mL) and saturated aqueous sodium chloride solution (5 mL) while adjusting the pH of the aqueous phase to 9.5 by addition of dilute hydrochloric acid. The mixture was shaken, the layers separated, and the aqueous portion was extracted with additional ethyl acetate (2×2.5 mL). The combined ethyl acetate solution was washed with brine (5 mL), dried over magnesium sulfate, filtered and evaporated under reduced pressure to afford a foam (442 mg). This material was shown by $^1$H NMR spectroscopy to consist of a 44:56 mixture of the (9E) and (9Z) isomers of 9-deoxo-9-hydroxyiminoerythromycin A.

Method 12: 1.0 LiOH in DMF

A mixture of (9E)-9-deoxo-9-hydroxyiminoerythromycin A (500 mg, 0.668 mmol), lithium hydroxide monohydrate (28 mg), and dimethylformamide (5 mL) was stirred at room temperature in a capped flask. After a few hours, the initial suspension gave way to a solution. After stirring for 18 days and 18 hours, the solution was evaporated under reduced pressure and the residue was processed as described in method 11 to afford a foam (402 mg). Analysis of this material by $^1$H NMR spectroscopy indicated a 62:38 mixture of the (9E) and (9Z) isomers of 9-deoxo-9-hydroxyiminoerythromycin A.

Method 13: 1.2 LiN(SiMe$_3$)$_2$ in MeCN

A suspension of (9E)-9-deoxo-9-hydroxyiminoerythromycin (500 mg, 0.668 mmol) in anhydrous acetonitrile (4 mL) was treated with lithium hexamethyldisilazide (0.80 mL of a 1M solution in hexane, 0.80 mmol). The resulting suspension rapidly gave way to a solution which reformed a suspension after stirring several days at room temperature. After 18 days and 19 hours, the reaction mixture was worked up as described in method 11 to afford a foam (423 mg). This material was shown by $^1$H NMR spectroscopy to be a 50:50 mixture of (9E)-9-deoxo-9-hydroxyiminoerythromycin A and (9Z)-9-deoxo-9-hydroxyiminoerythromycin A.

EXAMPLE 3

Crystallization of 9-Deoxo-9(Z)-hydroxyiminoerythromycin A

A 3:1 mixture (30.0 g) of (9Z)-9-deoxo-9-hydroxyiminoerythromycin A and 9-deoxo-9-(9E)-hydroxyiminoerythromycin A was added over 2 minutes to well stirred ethyl acetate (60 mL). After obtaining a solution, methylene chloride (120 mL) was rapidly added and the resulting suspension was stirred in an ice bath for one hour. The precipitate was filtered off, washed with methylene chloride (60 mL), and dried under a stream of nitrogen to afford an 86:14 mixture (26.5 g) of of (9Z)-9-deoxo-9-hydroxyiminoerythromycin A and (9E)-9-deoxo-9-hydroxyiminoerythromycin A.

A solution of the above solid in ethyl acetate (60 mL) was diluted with methylene chloride (120 mL). The resulting suspension was cooled in an ice bath for one hour and then filtered. The collected solid was rinsed with methylene chloride (60 mL) and dried under a stream of nitrogen to afford a 95:5 mixture (23.4 g) of (9Z)-9-deoxo-9-hydroxyiminoerythromycin A and (9E)-9-deoxo-9-hydroxyiminoerythromycin A.

EXAMPLE 4

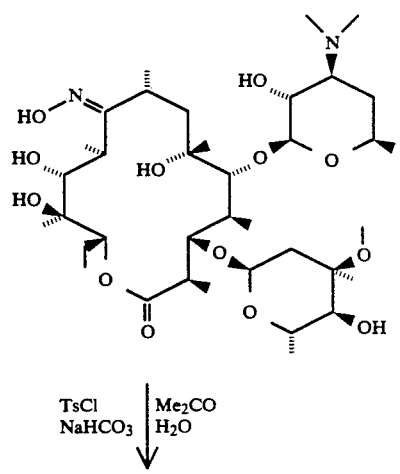

TsCl  Me$_2$CO
NaHCO$_3$  H$_2$O

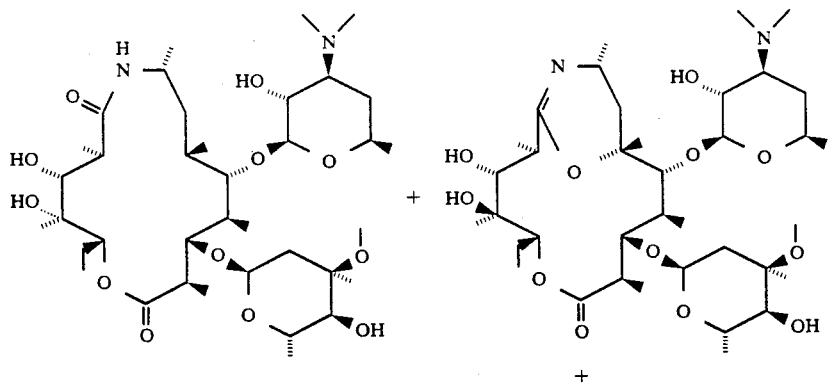

+

Synthesis of 8a-Aza-8a-homoerythromycin A and 9-Deoxo-6-deoxy-6,9-epoxy-8a,9-didehydro-8a-aza-8a-homoerythromycin A by the Beckmann Rearrangement of (9Z)-9-Deoxo-9-hydroxyiminoSthromycin A Method 1

(9Z)-9-Deoxo-9-hydroxyiminoerythromycin A (200 mg, 0.27 mMol) was dissolved in acetone (2 mL) and the resulting solution was cooled in an ice-bath and stirred under a nitrogen atmosphere. A solution of sodium bicarbonate (84 mg, 1.0 mMol) in water (2 mL) was added followed by the dropwise addition of an acetone solution (2 mL) of p-toluenesulfonyl chloride (100 mg, 0.53 mMol) over 5 minutes.

After stirring for 1.5 hours at 0°-5° C., the mixture was diluted with dichloromethane (10 mL) and water (5 mL), and the pH was adjusted from 10 to 5.5 with 2N HCl. The dichloromethane layer was discarded and the aqueous layer was washed with additional dichloromethane (2×10 mL) which was also discarded. Dichloromethane (10 mL) was added to the aqueous layer and the pH was adjusted to 8.5 with 2.5N NaOH. The dichloromethane layer was removed and the aqueous layer was extracted with more dichloromethane (2×20 mL). The combined dichloromethane extracts were dried over anhydrous magnesium sulfate, filtered and evaporated under vacuum to give a mixture of the title compounds as a foam (150 mg).

The above mixture was purified by preparative layer chromatography (two 0.1 mm×20×20 cm Analtech silica gel GF plates, developing and eluting with 60:10:1 dichloromethane-methanol concentrated ammonium hydroxide) to afford 8a-aza-8a-homoerythromycin A (95 mg) and 9-deoxo-6-deoxy-6,9-epoxy-8a,9-didehydro-8a-aza-8a-homoerythromycin A (33 mg).

Method 2

A solution of p-toluenesulfonyl chloride (1.00 g, 5.2 mmol) in acetone (20 mL) was added to a solution of sodium bicarbonate (0.90 g, 10.7 mmol) in water (20 mL). The resulting suspension was cooled in a −10° C. bath and stirred while a solution of (9Z)-9-deoxo-9-hydroxyiminoerythromycin A (2.00 g, 2.7 mmol) in acetone (20 mL) was added slowly over 75 minutes. The mixture was stirred at −10° C. for 5 hours, then warmed to 0° C. over 10 minutes and stirred at 0°-5° C. for 30 minutes. The mixture was evaporated under vacuum to remove the acetone. The aqueous residue was diluted with water (40 mL) and dichloromethane (60 mL) and stirred while the pH was adjusted to 5.5 with dilute hydrochloric acid. The aqueous layer was separated, washed with dichloromethane (60 mL), layered with dichloromethane (60 mL), and stirred while the pH was brought to 9 with dilute aqueous sodium hydroxide. The layers were separated and the aqueous portion extracted with more dichloromethane (2×50 mL). The combined pH 9 extracts were dried over magnesium sulfate, filtered and evaporated under reduced pressure to afford a gum (1.97 g) which was shown by $^1$H NMR spectroscopy to be a 1:1 mixture of 8a-aza-8a-homoerythromycin A and 9-deoxo-6-deoxy-6,9-epoxy-8a,9-didehydro-8a-aza-8a-homoerythromycin A.

The crude product mixture was dissolved in 120:10:1 dichloromethane-methanol-conc. aqueous ammonium-hydroxide (5 mL) and loaded onto a column of silica gel (4×16 cm). The column was eluted with 120:10:1 dichloromethane methanol-ammonium hydroxide. After a 150 mL forerun, 15 mL fractions were collected. Fractions 9-13 were combined and evaporated under vacuum to afford 9-deoxo-6-deoxy-6,9-epoxy-8a,9-didehydro-8a-aza-8a-homoerythromycin A (ca. 500 mg) and fractions 22-26 were combined and evaporated to afford 8a-aza-8a-homoerythromycin A (ca. 500 mg). The later product was crystallized from ether to give the amide (ca. 130 mg) as a white solid.

Physical data for 9-deoxo-6deoxy-6,9-epoxy-8a,9-didehydro-8a-aza-8a-homoerythromycin A IR (CHCl$_3$) 3550, 3440 (br), 2970, 2940, 3880, 1725, 1665, 1455, 1375, 1345, 1325, 1240, 1170, 1105, 1080, 1050, 1015, 995, and 955 cm−1.

$^1$H NMR (CDCl$_3$) δ 5.02 (d, H—1″), 4.90 (dd, H—13), 4.48 (d, H—1′), 4.09 (dq, H—5″), 4.02 (t, H—3), 3.81 (d, H—5), 3.53 (m, H—5′), 3.49 (d, H—11), 3.43 (m, H—8), 3.35 (s, OCH$_3$), 3.20 (dd, H—2′), 3.07 (t, H—4″), 2.75 (dq, H—2), 2.68 (dq, H—10), 2.52 (ddd, H—3′), 2.43 (d, H—2″eq), 2.28 (s, N(CH$_3$)2), 1.98 (ddq, H—4), 1.91 (m, H—14a), 1.90 (dd, H—7a), 1.68 (ddd, H—4′eq), 1.62 (dd, H—2″ax), 1.46 (m, H—14b), 1.39 (s, 6—CH$_3$), 1.32 (d, 5″—CH$_3$), 1.27 (s, 3″—CH$_3$), 1.24 (m, H—7b), 1.22 (d, 5′—CH$_3$), 1.21 (m, H—4′ax), 1.16 (d, 10—CH$_3$), 1.15 (d, 8—CH$_3$), 1.15 (s, 12—CH$_3$), 1.14 (d, 2—CH$_3$), 1.08 (d, 4—CH$_3$), and 0.87 (t, CH$_2$CH$_3$).

$^{13}$C NMR (CDCl$_3$) δ 177.6, 160.6, 102.4, 94.6, 80.1, 78.9, 77.9, 77.4, 76.5, 75.7, 73.0, 70.6, 70.0, 68.8, 65.8, 65.6, 49.4, 44.9, 44.0, 42.3, 42.1, 40.3, 34.5, 32.0, 28.5, 23.8, 22.4, 21.5, 21.3, 21.0, 18.2, 17.0, 16.4, 12.5, 10.8, and 8.4.

FAB mass spectrum, m/e 731, 713, 602, 573, 555, 398, 159, 158, and 116.

Physical data for 8a-aza-8a-homoerythromycin A

MP 170°-176° C.

IR (CHCl$_3$) 3500 (br), 3430, 3320, 2970, 2935, 2880, 1730, 1630, 1560, 1525, 1455, 1375, 1325, 1280, 1170, 1160, 1105, 1085, 1045, 1010 and 995 cm$^{-1}$.

$^1$H NMR (CDCl$_3$) δ 5.89 (br d, NH), 5.07 (d, H—1″), 4.92 (dd, H—13), 4.43 (d, H—1′), 4.32 (d, H—3), 4.21 (m, H—8), 4.01 (dq, H—5″), 3.58 (d, H—5), 3.50 (m, H—5′), 3.50 (s, H—11), 3.32 (s, OCH$_3$), 3.21 (dd, H—2′), 3.03 (t, H—4″), 2.62 (dq, H—2), 2.54 (m, H—3′), 2.35 (m, H—10), 2.35 (s, N(CH$_3$)$_2$), 2.31 (d, H—2″eq), 1.90 (m, H—4), 1.89 (m, H—14a), 1.75 (br d, H—4′eq), 1.57 (dd, H—2″ax), 1.51 (m, H—7a and H—7b), 1.44 (m, H—14b), 1.43 (s, 6—CH$_3$), 1.30 (d, 5″—CH$_3$), 1.24 (s, 3″—CH$_3$), 1.23 (m, H—4′ax), 1.23 (d, 5′—CH$_3$), 1.20 (d, 8—CH$_3$), 1.19 (d, 10—CH$_3$), 1.18 d, 2—CH$_3$) 1.09 s, 12—CH$_3$), 1.05 (d, 4—CH$_3$), and 0.89 (t, CH$_2$CH$_3$).

$^{13}$C NMR (CDCl$_3$) δ 177.6, 176.6, 102.7, 94.2, 83.0, 77.9, 77.0, 76.6, 74.6, 73.7, 72.9, 70.0, 69.8, 68.8, 65.8, 65.2, 49.2, 45.8, 43.2, 42.4, 41.0, 40.4, 40.1, 34.5, 28.3, 27.6, 23.1, 21.7, 21.5, 21.2, 18.0, 16.1, 14.6, 11.2, 10.0, and 9.1.

mass spectrum, m/e 749, 731, 591, 589, 573, 416, 174, 159, 158 and 117.

Elemental Analysis.

Calculated for C$_{37}$H$_{68}$N$_2$O$_{13}$: C, 59.34; H, 9.15; N, 3.74.

Found: C, 59.24; H, 9.15; N, 3.44. Loss on drying at 120° C., 3.11%.

EXAMPLE 5

Synthesis of 9-Deoxo-6deoxy-6,9-epoxy-8a,9-didehydro-8a-aza-8a-homoerythromycin A and 9-Deoxo-12-deoxy-9,12-epoxy-8a,9-didehydro-8a-aza-8a-homoerythromycin A by Beckmann Rearrangement of (9Z)-9-hydroxyiminoerythromycin A

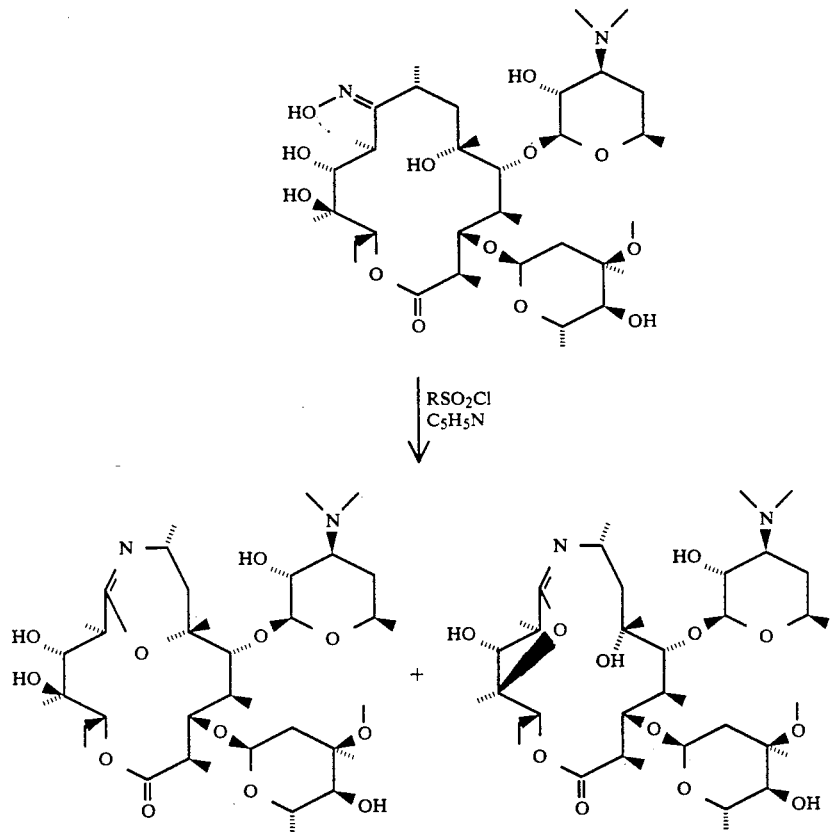

Method 1

A solution of p-toluenesulfonyl chloride (15.0 g, 0.079 mol) in diethyl ether (50 mL) was added dropwise over 8 minutes to an ice-cold, stirring solution of (9Z)-9-deoxo-9-hydroxyiminoerythromycin A (23.2 g, 0.031 mol) in pyridine (180 mL). The resulting solution was stirred at 0°-5° C. for 2.5 hours, then diluted with dichloromethane (400 mL) and water (500 mL) and basified to pH 9.5 by addition of 5N sodium hydroxide. The layers were separated and the aqueous portion extracted with more dichloromethane (200 mL, 100 mL). The combined dichloromethane extracts were dried over magnesium sulfate, filtered, and evaporated under vacuum to afford an oil. Residual pyridine was removed by twice taking the product up in toluene (100 mL) and evaporating the solvent under vacuum. The resulting foam (21.4 g) was shown by $^1$H NMR spectroscopy to be a 26:74 mixture of 9-deoxo-6-deoxy-6,9-epoxy-8a,9-epoxy-8a,9-didehydro-8a-aza-8a-homoerythromycin A and 9-deoxo-12-deoxy-9,12-epoxy-8a,9-didehydro-8a-aza-8a-homoerythromycin A.

Method 2

A solution of p-toluenesulfonyl chloride (160 mg, 0.84 mmol) in diethyl ether (0.5 mL) was added rapidly to an ice-cold solution of (9Z)-9-deoxo-9-hydroxyiminoerythromycin A (250 mg, 0.33 mmol) in pyridine (2.0 mL). The resulting solution was stirred at 0°-5° C. for 1.5 hours, then diluted with dichloromethane (4 mL) and water (4 mL) and basified to pH 9.5 by addition of 5N sodium hydroxide. The layers were separated and the aqueous portion extracted with more dichloromethane (2×4 mL). The combined dichloromethane extracts were dried over magnesium sulfate, filtered, evaporated under vacuum and stripped with hexane (4×15 mL) to afford a yellow solid (260 mg). This material was shown by 1H NMR spectroscopy to be a 25:75 mixture of 9-deoxo-6-deoxy-6,9-epoxy- and 9-deoxo-12-deoxy-9,12-epoxy-8a,9-didehydro-8a-aza-8a-homoerythromycin

Method 3

A solution of p-toluenesulfonyl chloride (160 mg, 0.84 mmol) in acetonitrile (0.5 mL) was added rapidly to an ice-cold solution of (9Z)-9-deoxo-9-hydroxyiminoerythromycin A (250 mg, 0.33 mmol) in pyridine (2.0 mL). The resulting solution was stirred at 0°-5° C. for 80 minutes, then diluted with dichloromethane (4 mL) and water (5 mL) and basified to pH 9.5 by addition of 5N sodium hydroxide. The layers were separated and the aqueous portion extracted with more dichloromethane (2×4 mL). The combined dichloromethane extracts were dried over magnesium sulfate, filtered, and evaporated under vacuum to a foam which was stripped with toluene (2×10 mL) and hexanes (10 mL) to afford a solid (230 mg). This material was shown by 1H NMR spectroscopy to be a 33:67 mixture of 9-deoxo-6-deoxy-6,9-epoxy- and 9-deoxo-12-deoxy-9,12-epoxy-8a,9-didehydro-8a-aza-8a-homoerythromycin A.

Method 4

A solution of p-toluenesulfonyl chloride (160 mg, 0.84 mmol) in toluene (0.5 mL) was added rapidly to an ice-cold solution of (9Z)-9-deoxo-9-hydroxyiminoerythromycin A (250 mg, 0.33 mmol) in pyridine (2.0 mL). The resulting solution was stirred at 0°-5° C. for 90 minutes, then diluted with dichloromethane (4 mL) and water (4 mL) and basified to pH 9.5 by addition of 1N sodium hydroxide. The layers were separated and the aqueous portion extracted with more dichloromethane (3×4 mL). The combined dichloromethane extracts were dried over magnesium sulfate, filtered, and evaporated under vacuum to a solid (250 mg). This material was shown by 1H NMR spectroscopy to be a 27:73 mixture of 9-deoxo-6-deoxy-6,9-epoxy- and 9-deoxo-12-deoxy-9,12-epoxy-8a,9-didehydro-8a-aza-8a-homoerythromycin A.

Method 5

Benzenesulfonyl chloride (0.107 mL, 0.84 mmol) was added by syringe to an ice-cold solution of (9Z)-9-deoxo-9-hydroxyiminoerythromycin A (250 mg, 0.33 mmol) in pyridine (2.0 mL). The resulting solution was stirred at 0°-5° C. for 75 minutes, the processed as described above to afford a yellow solid (240 mg). This material was shown by 1H NMR spectroscopy to be a 31:69 mixture of 9-deoxo-6-deoxy-6,9-epoxy- and 9-deoxo-12-deoxy-9,12-epoxy-8a,9-didehydro-8a-aza-8a-homoerythromycin A.

Method 6

Methanesulfonyl chloride (0.065 mL, 0.84 mmol) was added by syringe to an ice-cold solution of (9Z)-9-deoxo-9-hydroxyiminoerythromycin A (250 mg, 0.33 mmol) in pyridine (2.0 mL). The resulting solution was stirred at 0°-5° C. for 2 hours, then processed as described above to afford an off-white solid (246 mg). This material was shown by 1H NMR spectroscopy to be a 25:70:5 mixture of 9-deoxo-6-deoxy-6,9-epoxy-8a,9-didehydro-8a-aza-8a-homoerythromycin A, 9-deoxo-12-deoxy-9,12-epoxy-8a,9-didehydro-8a-aza-8a-homoerythromycin A, and 9-deoxy-12-deoxy-9,12-epoxy-4″-O-methanesulfonyl-8a,9-didehydro-8a-aza-8a-homoerythromycin A.

Method 7

A solution of (9Z)-9-deoxo-9(Z)-hydroxyiminoerythromycin A (250 mg, 0.33 mmol) in pyridine (2.0 mL) was cooled in a −20° C. bath and treated with methanesulfonyl chloride (0.071 mL, 0.92 mmol). The resulting hazy solution was stirred at −10° to −20° C. for 90 minutes, then processed as described above to afford a yellow solid (254 mg). This material was shown by 1H NMR spectroscopy to be a 88:12 mixture of 9-deoxo-6-deoxy-6,9-epoxy-8a,9-didehydro-8a-aza-8a-homoerythromycin A and 9-deoxo-12-deoxy-9,12-epoxy-8a,9-didehydro-8a-aza-8a-homoerythromycin A.

Method 8

A mixture of (9Z)-9-deoxo-9-hydroxyiminoerythromycin A (0.50 g, 0.67 mmol), p-toluenesulfonyl chloride (318 mg, 1.67 mmol) and pyridine (0.162 mL, 2.0 mmol) in dichloromethane (5.0 mL) was stirred at room temperature for 1.5 hours. The mixture was diluted with water and stirred rapidly while adjusting the pH to 11 with 5N sodium hydroxide. The organic phase was separated, dried with magnesium sulfate, filtered and evaporated under reduced pressure to afford a yellow solid (570 mg). Analysis of the crude product by 1H NMR spectroscopy revealed a 80:20 mixture of 9-deoxo-6-deoxy-6,9-epoxy-8a,9-didehydro-8a-aza-8a-homoerythromycin A and 9-deoxo-12-deoxy-9,12-epoxy-8a,9-didehydro-8a-aza-8a-homoerythromycin A.

EXAMPLE 6

Purification of 9Deoxo-12-9,12-epoxy-8a,9-didehydro-8a-aza-8a-homoerythromycin A by Column Chromatography Although unnecessary for the following reduction step, it is possible to separate the isomeric 6,9-epoxy- and 9,12-epoxy products by silica gel or alumina column chromatography. The following procedure illustrates the purification process for 9-deoxo-12-deoxy-9,12-epoxy-8a,9-didehydro-8a-aza-8a-homoerythromycin A.

The crude products from methods 3 and 4 above were combined, dissolved in 94:5:1 dichloromethane-methanol-triethylamine, and loaded onto a column of silica gel (230-400 mesh, 2.5×24.5 cm, wet packed under 94:5:1 dichloromethane-methanol-triethylamine). The column was eluted with 94:5:1 dichloromethane-methanol-triethylamine, collecting 6 mL fractions. Fractions 15-18 were combined, evaporated under reduced pressure, and the residue twice stripped with toluene to provide 9-deoxo-12-deoxy-9,12-epoxy-8a,9-didehydro-8a-aza-8a-homoerythromycin A (190 mg) as a foam. The product is a mixture of a major and minor forms, as ascertained by $^1$H and $^{13}$C NMR spectroscopy.

IR (CHCl$_3$) 3550, 3390 (br), 2975, 2940, 2880, 1735, 1690, 1455, 1375, 1240, 1165, 1085, 1045, 1010, and 970 cm$^{-1}$.

FAB mass spectrum, m/e 731, 713, 602, 573, 556, and 158.

EXAMPLE 7

Chromatographic Separation of 9-Deoxo-6-deoxy-6,9-epoxy-8a,9-didehydro-8a-aza-8a-homoerythromycin A and 9-Deoxo-12deoxy-9,12-epoxy-8a,9-didehydro-8a-aza-8a-homoerythromycin A and Crystallization of 9Deoxo-12deoxy-9,12-epoxy-8a,9-didehydro-8a-aza-8a-homoerythromycin A A sample (4.0 g) of the crude product mixture obtained as described in method 1 was dissolved in 60:10:1 dichloromethane-methanol-conc. aqueous ammonium hydroxide (6 mL) and the solution was loaded onto a column of EM silica gel 60 (4.5×18 cm, 230-400 mesh, wet packed under 60:10:1 dichloromethane-methanol-conc. ammonium hydroxide). The column was eluted with 60:10:1 dichloromethane-methanol-conc. aqueous ammonium hydroxide. The fractions collected from 150 mL to 165 mL of eluant were evaporated under vacuum to afford 9-deoxo-6-deoxy-6,9-epoxy-8a,9-didehydro-8a-aza-8a-homoerythromycin A (0.34 g) as a foam. The fractions collected from 185 mL to 285 mL of eluant were combined and evaporated under reduced pressure to afford a mixture of the two isomeric forms of 9-deoxo-12-deoxy-9,12-epoxy-8a,9-didehydro-8a-aza-8a-homoerythromycin A (1.36 g) as a foam.

A solution of the mixture of 9,12-epoxy isomers in nitromethane (2 mL) deposited a large, crystalline mass on standing at room temperature for several days. The mixture was diluted with nitromethane (10 mL) and filtered to remove the solid portion, which was washed with nitromethane (2 mL) and dried under high vacuum. The white solid thus obtained (0.9 g) was shown by $^1$H NMR spectroscopy to be the major 9,12-epoxy isomer which is initially formed in the Beckmann rearrangement reaction. While stable in the solid state, solutions of the crystalline isomer in chloroform-d isomerize at room temperature in several hours to a 1:1 mixture of the two isomers of 9-deoxo-12-deoxy-6,9-epoxy-8a,9-didehydro-8a-aza-8a-homoerythromycin A.

Physical data for 9-deoxo-12-deoxy-9,12-epoxy-8a,9-didehydro-8a-aza-8a-homoerythromycin A Isomer A (crystalline isomer)

MP 124°-130° C. (slowly softens).

IR (CHCl$_3$) 3550, 3380 (br), 2970, 2935, 2875, 1735, 1695, 1560, 1460, 1375, 1250, 1165, 1115, 1085, 1045, 1015, and 975 cm$^{-1}$.

$^1$H NMR (CDCl$_3$) δ 5.17 dd, H—13), 4.75 (d, H—1"), 4.47 (d, H—1'), 4.15 (dq, H—5"), 4.09 (dd, H—3), 3.99 br s, H—5), 3.81 (t, H—11), 3.68 (m, H—8), 3.65 (m, H—5'), 3.40 (ddd, H—2'), 3.23 (s, OCH$_3$), 2.96 t, H—4"), 2.70 (p, H—10), 2.68 (m, H—3'), 2.57 (br d, 11—OH), 2.45 (p, H—2), 2.31 (s, N(CH$_3$)$_2$), 2.28 (d, H—2"eq), 2.20 (d, 4"—OH), 2.07 (ddq, H—14a), 1.90 (br d, H—7a), 1.75 (dd, H—7b), 1.74 (m, H—4), 1.70 (m, H—4'eq), 1.69 (m, H—14b), 1.46 (dd, H—2"ax), 1.40 (s, 6—CH$_3$), 1.29 (m, H—4'ax), 1.27 (d, 10—CH$_3$), 1.27 (d, 5"CH$_3$), 1.25 (d, 2—CH$_3$), 1.24 (d, 5'—CH$_3$), 1.21 (s, 3"—CH$_3$), 1.18 (s, 12—CH$_3$), 1.07 (d, 8—CH$_3$), 1.01 (d, 4—CH$_3$), and 0.86 (t, CH$_2$C$\underline{H}_3$).

$^{13}$C NMR (CDCl$_3$) δ 174.2, 161.3, 106.7, 98.3, 85.4, 84.2, 80.5, 79.8, 77.4, 75.0, 72.3, 72.3, 70.3, 69.4, 66.3,, 63.8, 49.4, 49.2, 49.0, 47.1, 45.4, 43.2, 40.4, 35.0, 29.3, 27.5, 24.6, 24.4, 23.3, 21.4, 21.0, 17.6, 17.2, 16.9, 11.3, and 11.2.

Elemental Analysis. Calculated for C$_{37}$H$_{66}$N$_2$O$_{12}$: C, 60.80; H, 9.10; N, 3.83. Found: C, 60.71; H, 9.38; N, 3.78. Loss on drying at 120° C., 2.82%.

Isomer B $^1$H NMR (CDCl$_3$) δ 5.20 (dd, H—13), 4.74 (d, H—1"), 4.48 (d, H—1'), 4.17 (t, H—3), 4.15 (m, H—5"), 4.11 (dd, H—11), 3.97 (m, H—8), 3.71 (d, H—5), 3.62 (m, H—5'), 3.30 (br dd, H—2'), 3.23 (s, OCH$_3$), 2.97 (t, H—4"), 2.88 (d, 11—OH), 2.85 (p, H—10), 2.60 (m, H—3'), 2.46 (p, H—2), 2.28 (s, N(CH$_3$)$_2$), 2.27 (d, H—2'-eq), 2.23 (d, 4"—OH), 1.98 (ddq, H—14a), 1.82 (dd, H—7a), 1.77 (m, H—4), 1.76 (m, H—14b), 1.66 (m, H—4'eq), 1.64 (dd, H—7b), 1.49 (dd, H—2"ax), 1.29 (s, 6—CH$_3$), 1.27 (d, 5"—CH$_3$), 1.24 (m, H—4'ax), 1.24 (d, 2—CH$_3$), 1.22 (d, 5'—CH$_3$), 1.19 (d, 10—CH$_3$), 1.19 (s, 3'—CH$_3$), 1.14 (s, 12—CH$_3$), 1.09 (d, 8—CH$_3$), 1.09 (d, 4—CH$_3$), and 0.94 (t, CH$_2$C$\underline{H}_3$).

$^{13}$C NMR (CDCl$_3$) δ 174.4, 160.5, 104.6, 97.0, 86.2, 79.1, 78.6, 77.7, 77.4, 75.1, 70.5, 69.4, 66.0, 64.7, 49.4, 48.2, 47.7, 47.4, 42.3, 40.4, 34.9, 29.1, 25.6, 24.0, 23.6, 22.9, 21.5, 21.0, 15.8, 11.7, 10.7, and 9.6.

EXAMPLE 8

Synthesis of 9Deoxo-8a-aza-8a-homoerythromycin A by Sodium Borohydride Reduction of 9-Deoxo-6-deoxy-6,9-epoxy-8a,-didehydro-8a-aza-8a-homoerythromycin A and 9-Deoxo-12-deoxy-9,12-epoxy-8a,9-didehydro-8a-aza-8a-homoerythromycin A filtered and evaporated under reduced pressure to a foam (15.4 g).

The crude product was dissolved in 2-propanol (90 mL) and stirred at room temperature to give a crystalline precipitate. This material was collected, washed with cold 2-propanol (20 mL) and dried to afford 9-deoxo-8a-aza-8a-homoerythromycin A (6.0 g) as a white solid.

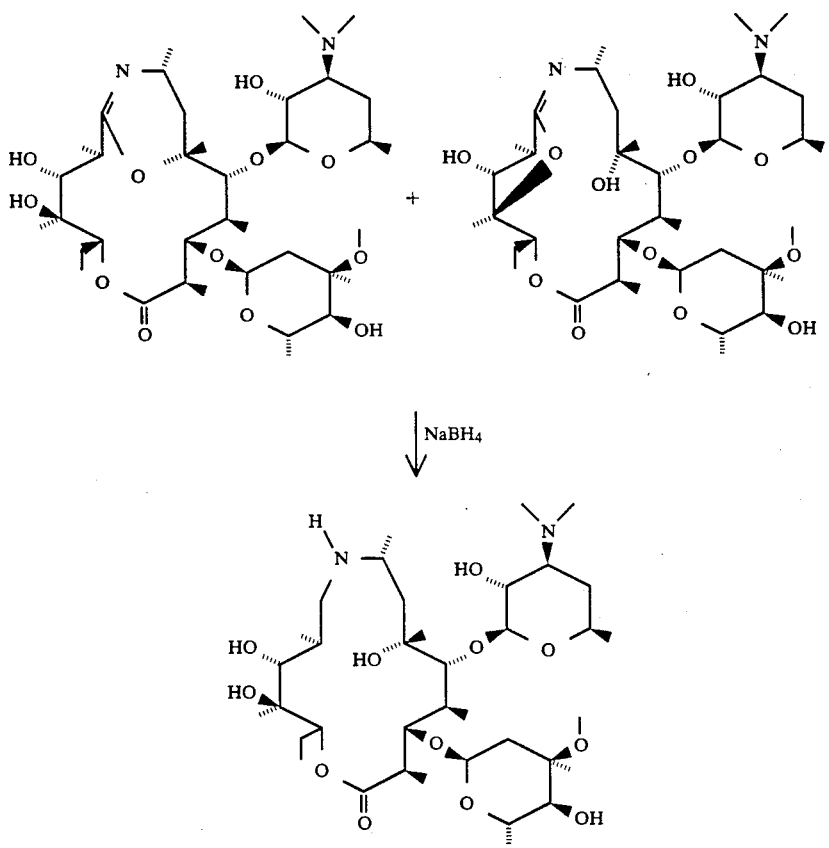

Method 1

A solution of 9-deoxo-6-deoxy-6,9-epoxy-8a-9-didehydro-8a-aza-8a-homoerythromycin A and 9-deoxo-12-deoxy-9,12-epoxy-8a,9-didehydro-8a-aza-8a-homoerythromycin A (22.6 g of a 27:73 mixture, 0.031 mol) in methanol (50 mL) was cooled in an ice bath and stirred under a nitrogen atmosphere. Solid sodium borohydride (3.6 g, 0.093 mol) was added in portions over 3 hours. The resulting viscous solution was allowed to slowly warm to room temperature and then stirred at room temperature overnight. The solution was diluted with water (50 mL), acidified to pH 2 with 2N hydrochloric acid, and stirred at room temperature for 10 minutes. The solution was diluted with water (150 mL) and dichloromethane (200 mL) and stirred vigorously while the pH was brought to 6.5 by addition of 5N sodium hydroxide. The dichloromethane layer was discarded and the aqueous phase layered with fresh dichloromethane, stirred rapidly and basified to pH 9.5 with 5N sodium hydroxide. The layers were separated and the aqueous portion extracted with more dichloromethane (2×100 mL). The combined pH 9.5 dichloromethane extracts were dried over magnesium sulfate, The mother liquors and washings were evaporated under vacuum to a solid residue. The solid was suspended in water (50 mL), acidified to pH 2, and stirred at room temperature for 30 minutes. The mixture was diluted with water (50 mL) and dichloromethane (100 mL), then stirred vigorously while adjusting the pH to 6.5. The dichloromethane layer was discarded and replaced with fresh dichloromethane (100 mL). The mixture was stirred while the pH was adjusted to 9.5. The layers were separated and the aqueous phase was extracted with more dichloromethane (2×100 mL). The combined basic extracts were dried with magnesium sulfate, filtered and evaporated under vacuum to a foam (6.2 g). This material was dissolved in 2-propanol (30 mL) and the solution cooled in ice to give additional crystalline product. The solid was collected and dried to afford additional 9-deoxo-8a-aza-8a-homoerythromycin A (2.7 g).

MP 177°–180° C.

IR (CHCl$_3$) 3540, 3340 (br), 2970, 2930, 2880, 1725, 1450, 1375, 1325, 1125, 1105, 1085, 1065, 1045, 955, and 870 cm$^{-1}$.

$^1$H NMR (CDCl$_3$) δ 5.00 (d, H—1″), 4.75 (dd, H—13), 4.48 (br d, H—3), 4.34 (d, H—1′), 4.02 (dq, H—5″), 3.56 (br s, H—11), 3.52 (d, H—5), 3.45 (m,

H—5'), 3.31 (s, OCH₃), 3.16 (dd, H—2'), 3.01 (br d, H—4"), 2.78 (m, H—8), 2.69 (dq, H—2), 2.59 (dd, H—9a), 2.42 (br t, H—9b), 2.30 (d, H—2"eq), 2.26 (s, N(CH₃)₂), 1.91 (m, H—14a), 1.77 (br p, H—4), 1.61 (br d, H—4'eq), 1.55 (dd, H—2"ax), 1.44 (m, H—14b), 1.38 (m, H—7), 1.36 (s, 6—CH₃), 1.29 (d, 5"—CH₃), 1.21 (s, 3"—CH₃), 1.20 (d, 5'—CH₃), 1.18 (d, 2—CH₃), 1.10 (d, 8—CH₃), 1.06 (s 12—CH₃), .104 (d, 4—CH₃), 0.94 (d, 10—CH₃), and 0.86 (t, CH₂CH₃).

¹³C NMR (CDCl₃) δ 178.6, 103.4, 94.6, 83.6, 78.1, 77.6, 76.6, 74.9, 72.8, 70.7, 68.9, 66.8, 65.7, 65.2, 49.6, 49.4, 45.5, 43.4, 40.3, 35.3, 34.7, 28.7, 27.6, 21.6, 21.3, 20.8, 18.2, 16.3, 15.1, 12.1, 11.3, and 9.5.

FAB mass spectrum, m/e 735, 577, 559, 402, 159, 158, and 116.

Elemental Analysis. Calculated for $C_{37}H_{70}N_2O_{12}$: C, 60.47; H, 9.60; N, 3.81. Found C, 59.98; H, 9.46; N, 3.62. Loss on drying at 120° C., 0.33%.

Method 2

A solution of 9-deoxo-6-dexoy-6,9-epoxy-8a,9-didehydro-8a-aza-8a-homoerythromycin A and 9-deoxo-12-deoxy-9,12-epoxy-8a,9-didehydro-8a-aza-8a-homoerythromycin A (5.0 g of a 1:3 mixture, 6.84 mmol) in ethylene glycol (25 mL) was cooled in an ice bath and stirred under a low stream of nitrogen. Sodium borohydride (0.60 g, 15.86 mmol) was added in two nearly equal portions spaced one hour apart. Following the borohydride addition, the reaction mixture was stirred at 0°-5° C. for 1.5 hours, then warmed to room temperature and stirred at room temperature overnight. The reaction mixture was diluted with water (50 mL) and dichloromethane (25 mL), stirred vigorously, and the phases separated. The aqueous portion was extracted with more dichloromethane (4×25 mL). The combined organic extracts were washed with brine (50 mL), dried over magnesium sulfate, filtered and evaporated under reduced pressure to a foam (4.0 g).

The crude product was dissolved in 2-propanol (20 mL) and the solution stirred at room temperature to give a crystalline precipitate. The product was collected and dried under a stream of nitrogen to afford 9-deoxo-8a-aza-8a-homoerthromycin A (2.2 g) as a white solid.

EXAMPLE 9

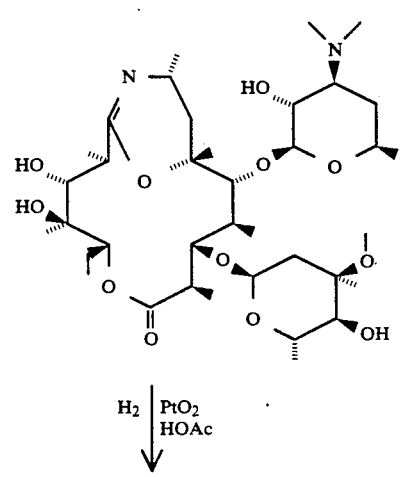

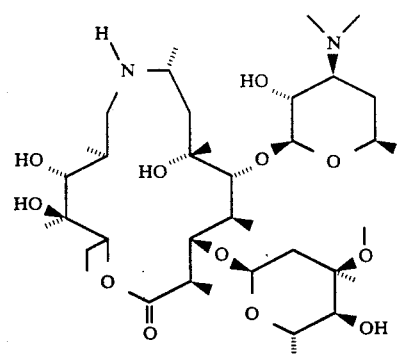

Synthesis of 9-Deoxo-8a-aza-8a-homoerythromycin A

A mixture of 9-deoxo-6-deoxy-6,9-epoxy-8a,9-didehydro-8a-aza-8a-homoerythromycin A (100 mg), acetic acid (4 mL) and platinum oxide (120 mg) was hydrogenated overnight at 2000 psi. The mixture was filtered through celite and the filtrate evaporated under a vacuum to a residue which was partitioned between dichloromethane (12 mL) and saturated sodium bicarbonate (5 mL). The dichloromethane was removed and the aqueous layer re-extracted with dichloromethane (2×5 mL). The combined methylene chloride extracts were dried over anhydrous magnesium sulfate, filtered and evaporated under vacuum to an oil (60 mg).

The oil was purified by preparative thin-layer chromatography (Analtech 0.1 mm×20×20 cm basic alumina plate, developing and eluting with 5% methanol in dichloromethane) to give the title compound as a white foam (42 mg, 42% yield).

EXAMPLE 10

Synthesis of 9-Deoxo-8a-aza-8a-methyl-8a-homoerythromycin A by Methylation of 9Deoxo-8a-aza-8a-homoerythromycin A

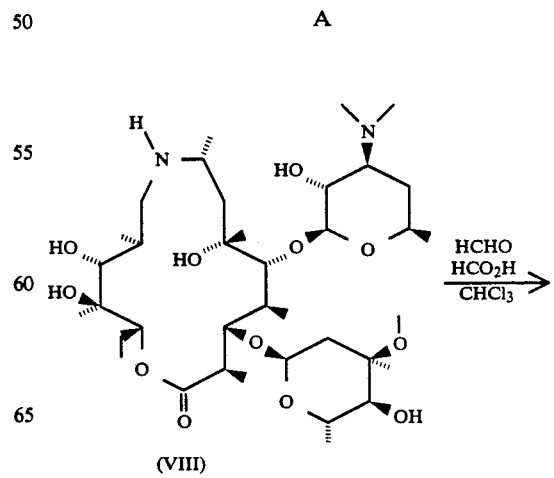

(VIII)

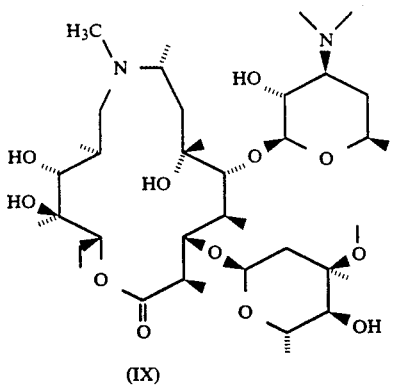

(IX)

A solution of 9-deoxo-8a-aza-8a-homoerythromycin A (7.30 g, 9.9 mmol) in chloroform (45 mL) was treated with 37% aqueous formaldehyde (0.81 mL, 10.8 mmol) and 98% formic acid (1.08 mL, 28.0 mmol). The resulting mixture was heated at reflux for 25.5 hours, then cooled to room temperature, diluted with dichloromethane (150 mL) and water (120 mL), and stirred vigorously for a few minutes. The dichloromethane layer was discarded and fresh dichloromethane (100 mL) was added. The mixture was stirred rapidly while the pH was adjusted to 9.5 by addition of 5N sodium hydroxide. The dichloromethane layer was removed and the aqueous portion was re-extracted with more dichloromethane (50 mL, 25 mL). The combined dichloromethane extracts were dried over anhydrous magnesium sulfate, filtered and evaporated under vacuum to a foam (7.27 g).

A solution of the foam in warm ethanol (24 mL) was diluted with water (12 mL) and stirred at room temperature for 5 minutes to give a precipitate. The mixture was diluted with more water (12 mL), stirred with ice-bath cooling, and then left in a refrigerator overnight. The mixture was filtered and the collected solid was rinsed with cold 3:1 water-ethanol (12 mL), dried under a stream of nitrogen and finally dried under vacuum to afford the title compound (6.20 g) as a white solid.

MP 187°–188° C.

IR (CHCl$_3$) 3540, 3330 (br), 2970, 2940, 2880, 2830, 1725, 1455, 1375, 1350, 1325, 1275, 1160, 1125, 1105, 1085, 1065, 1045, 995, 975, and 955 cm$^{-1}$.

$^1$H NMR (DCDl$_3$, 55° C.) δ 5.10 (d, H—1″), 4.86 (dd, H—13), 4.51 (t, H—3), 4.38 (d, H—1′), 4.04 (dq, H—5″), 3.53 (br s, H—11), 3.52 (d, H—5), 3.51 (m, H—5′), 3.32 (s, OCH$_3$), 3.23 (dd, H—2′), 3.01 (dd, H—4″), 2.99 (m, H—8), 2.81 (dq, H—2), 2.52 (m, H—9a), 2.40 (m, H—3′), 2.34 (s, N(CH$_3$)$_2$), 2.30 (m, H—9b), 2.30 (d, H—2″eq), 2.04 (s, NCH$_3$), 1.99 (m, H—10), 1.92 (m, H—14a), 1.88 (m, H—7a), 1.85 (m, H—4), 1.72 (br d, H—4′eq), 1.55 (dd, H—2″ax), 1.48 (m, H—14b), 1.37 (s, 6—CH$_3$), 1.30 (d, 5″—CH$_3$), 1.24 (d, 5′—CH$_3$), 1.23 (m, H—4′ax), 1.23 (s, 3″—CH$_3$), 1.19 (d, 2—CH$_3$), 1.12 (m, H—7b), 1.10 (d, 4—CH$_3$), 1.10 (s, 12—CH$_3$), 0.96 (d, 10—CH$_3$), 0.94 (d, 8—CH$_3$), and 0.92 (t, CH$_2$CH$_3$).

$^{13}$C NMR (CDCl$_3$, 55° C.) δ 178.3, 103.6, 94.7, 85.5, 78.4, 77.2, 76.7, 75.9, 74.9, 73.1, 71.0, 69.1, 67.1, 65.8, 65.4, 60.0, 56.7, 49.4, 45.8, 43.5, 40.4, 37.1, 35.1, 30.9, 29.3, 27.8, 22.1, 21.7, 21.3, 18.3, 16.4, 14.3, 12.7, 12.0, 11.4, and 11.3.

FAB mass spectrum, m/e 749, 591, 573, 158, and 116.

Elemental Analysis. Calculated for C$_{38}$H$_{72}$N$_2$O$_{12}$: C, 60.94; H, 9.69; N, 3.74. Found: C, 60.87; H, 9.39; N, 3.70. Loss on drying at 120° C., 0.74%.

EXAMPLE 11

Synthesis of 9-Deoxo-8a-aza-8a-methyl-8a-homoerythromycin A by Methylation of 9-Deoxo-8a-aza-8a-hydroxy-8a-homoerythromycin A 3′-N-Oxide

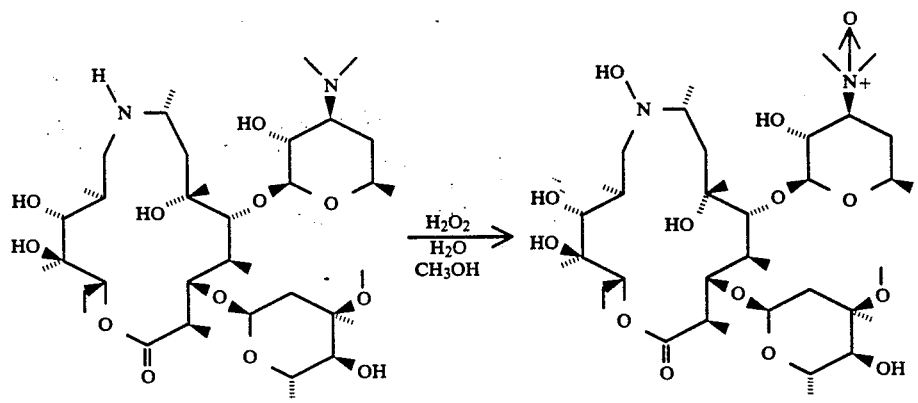

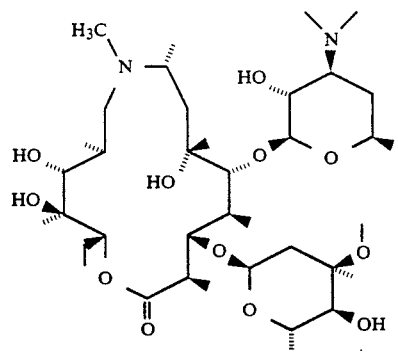

Step 1

9Deoxo-8a-aza-8a-hydroxy-8a-homoerythromycin A 3'-N-Oxide

9-Deoxo-8a-aza-8a-homoerythromycin A (385 mg, 0.524 mmol) in methanol (1.5 mL) was treated with 30% aqueous hydrogen peroxide (1.9 mL, 18.6 mmol) and the mixture was stirred at room temperature for 24 hours. The mixture was cooled in an ice bath, diluted with dichloromethane (10 mL) and water (8 mL), treated with saturated aqueous sodium sulfite (10 mL), and then stirred for 15 minutes to destroy excess oxidant. The phases were separated and the aqueous portion extracted with more dichloromethane (2×15 mL). The combined organic solution was dried with magnesium sulfate, filtered, and evaporated under reduced pressure to afford crude 9-deoxo-8a-hydroxy-8a-aza-8a-homoerythromycin A 3'-N-oxide (349 mg) as a white solid.

Step 2

9-Deoxo-8a-methyl-8a-aza-8a-homoerythromycin A

A portion of the product from step 1 (150 mg, 0.196 mmol) was dissolved in dichloromethane (3 mL) and the solution was treated with powdered anhydrous potassium carbonate (2.0 g, 14.5 mmol) and methyl iodide (0.5 mL, 8.0 mmol). The mixture was stirred at room temperature and under a nitrogen atmosphere for 3.5 hours. The mixture was filtered and the solids washed with dichloromethane (5 mL). Water (3 mL) was added to the combined filtrate and washings and the mixture was stirred vigorously while the pH was brought to 11 with 1N sodium hydroxide. The dichloromethane phase was dried with magnesium sulfate, filtered and evaporated under reduced pressure to afford a mixture of 9-deoxo-8a-methyl-8a-homoerythromycin A 3'-N-oxide and 9-deoxo-8a-methyl-8a-homoerythromycin A 8a-3'-N-bisoxide (136 mg) as a foam.

The crude product was dissolved in ethanol (6 mL), treated with 10% palladium on carbon (240 mg), and hydrogenated on a Parr shaker for 75 minutes at 45 psi. The mixture was filtered and the filtrate was evaporated under vacuum. The residue in dichloromethane (20 mL) was washed with saturated aqueous potassium carbonate, dried with magnesium sulfate, filtered, and evaporated under reduced pressure to provide 9-deoxo-8a-methyl-8a-homoerythromycin A (107 mg) as a foam.

The test procedures employed to measure this activity of the compounds of the invention are described below.

Example 12

The compounds of formula (II) show antibacterial activity against a range of aerobic Gram positive and negative bacteria, as shown in the following Table. The assay employs a liquid turbidimetric microtiter method for determination of the minimum inhibitory concentration (MIC) in broth media. The MIC endpoint in mcg/ml is defined as the lowest concentration of test compound that completely inhibits the growth (absence of detectable turbidity) of bacteria. The MIC is generally not an absolute value but rather a concentration range that falls within a two-fold dilution limit. Generally twelve two-fold dilutions of the test compound are employed with the initial concentration set at 128 mcg/ml.

TABLE I

In vitro Activity

| Microorganism | | MIC Values (mcg/ml) | |
|---|---|---|---|
| | | (VI) | (VII) |
| Enterococcus faecalis | MB 5407 | 32 | >128 |
| Enterococcus faecium | MB 5416 | 8 | 16 |
| Streptococcus agalactiae | CL 1343 | 1 | 4 |
| Staphylococcus aureus | MB 2865 | 16 | 16 |
| Staphylococcus epidermidis | MB 5414 | 32 | 16 |
| Staphylococcus haemolyticus | MB 5412 | 8 | 32 |
| Steptococcus pneumoniae | CL 2883 | 0.5 | 4 |
| Streptococcus pyogenes | MB 2874 | 1 | 2 |
| Streptococcus pyogenes | MB 5406 | 128 | >128 |
| Streptococcus viridans | CL 2943 | 16 | 4 |
| Escherichia coli | MB 2884 | 128 | 128 |
| Escherichia coli | MB 4926 | 8 | 32 |
| Klebsiella pneumoniae | MB 4005 | >128 | >128 |
| Yersinia enterocoltica | CL 1598 | 128 | NT |
| Pseudomonas stutzeri | MB 1231 | 0.5 | 2 |

Values given are for 9-Deoxo-6-deoxy-6,9-epoxy-8a,9-didehydro-8a-aza-8a-homoerythromycin A (VI) and 9-Deoxo-12-deoxy-9,12-epoxy-81,9-didehydro-8a-aza-8a-homoerythromycin A (VII).

The compounds of formula (II) are useful as an antibacterial agents both in vitro and in vivo, and their spectrum of activity is similar to that or erythromycin A. Consequently, they can be used for the same purposes, and, in the same manner, as erythromycin A. In general, the antibacterial compounds of formula II and salts thereof, exhibit in vitro activity against a variety of Gram-positive microorganisms, e.g. Streptococcus pyogenes, and against certain Gram-negative microorganisms such as those of spherical or ellipsoidal shape (cocci). Their activity is readily demonstrated by in vitro tests against various micro-organisms. Their in vitro activity renders them useful for topical application; for sterilization purposes, e.g., sick-room utensils; and as industrial antimicrobials, for example, in water treatment, slime control, and preservation of paint and wood. The extrapolation of such in vitro tests to support for such utilities for macrolide compounds is taught in U.S. Pat. No. 4,518,590, the entire disclosure of which is incorporated herein by reference. For in vitro use for topical application, it will usually be convenient to prepare pharmaceutical compositions, in which a compound is combined with a pharmaceutically-acceptable carrier or diluent, for example, in the form of ointments and creams. Appropriate carriers and diluents for these purposes include mineral oils and vegetable oils, and solvents such as water, alcohols, and glycols, and mixtures thereof. Such a pharmaceutical composition will normally contain the pharmaceutically-acceptable carrier and a compound of formula II in a weight ratio in the range from 1:4 to 1:200.

Additionally, the antibacterial compounds of formula II, and the pharmaceutically-acceptable salts thereof are active in vivo versus a variety of Gram-positive microorganisms, e.g. *Streptococcus pyogenes,* and also certain Gram-negative microorganisms, via the oral and parenteral routes of administration in animals, including man. Their in vivo activity is more limited than their in vitro activity as regards susceptible organisms, and it is determined by the usual procedure which comprises infecting mice of substantially uniform weight with the test organism and subsequently treating them orally or subcutaneously with the test compound. Extrapolation of such in vivo tests to support for human utility for macrolide compounds is likewise taught in U.S. Pat. No. 4,518,590, cited above.

While the invention has been described, exemplified and illustrated in reference to certain preferred ;embodiments thereof, those skilled in the art will appreciate that various changes, modifications and substitutions can be made therein without departing from the spirit and scope of the invention.

It is intended, therefore, that the invention be limited only by the scope of the claims which follow and that such claims be interpreted as broadly as is reasonable.

What is claimed is:

1. Compounds of the formulae:

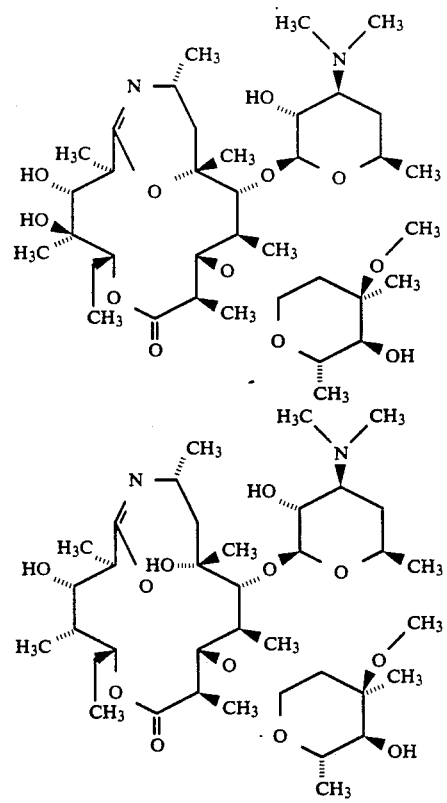

or a pharmaceutically acceptable salts thereof.

2. A compound of the formula:

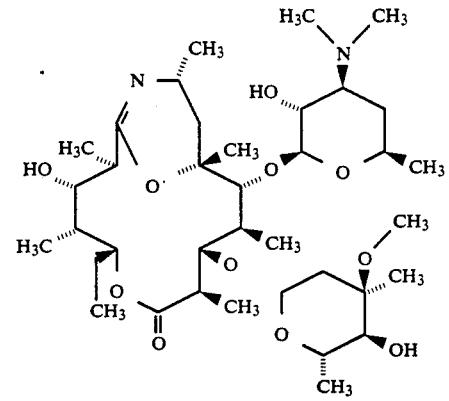

and the pharmaceutically acceptable salts thereof.

3. A compound of the formula:

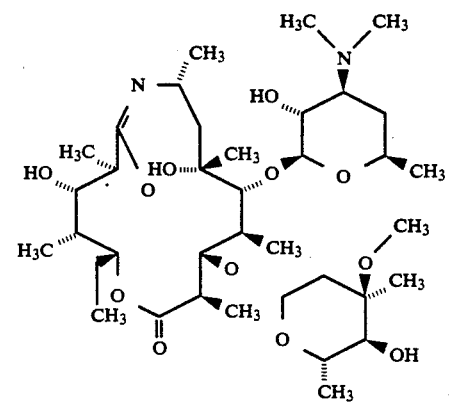

and the pharmaceutically acceptable salts thereof.

* * * * *